US009345760B2

(12) United States Patent
Dhar

(10) Patent No.: US 9,345,760 B2
(45) Date of Patent: May 24, 2016

(54) IPNV-ISAV BIVALENT VACCINE USING A VIRUS-LIKE PARTICLE-BASED PLATFORM AND METHODS OF USING THE SAME

(75) Inventor: Arun K. Dhar, Sykesville, MD (US)

(73) Assignee: Advanced Bionutrition Corporation, Columbia, MD (US)

( * ) Notice: Subject to any disclaimer, the term of this patent is extended or adjusted under 35 U.S.C. 154(b) by 0 days.

(21) Appl. No.: 14/343,666

(22) PCT Filed: Sep. 7, 2012

(86) PCT No.: PCT/US2012/054125
§ 371 (c)(1),
(2), (4) Date: May 29, 2014

(87) PCT Pub. No.: WO2013/036745
PCT Pub. Date: Mar. 14, 2013

(65) Prior Publication Data
US 2014/0314858 A1    Oct. 23, 2014

Related U.S. Application Data

(60) Provisional application No. 61/533,020, filed on Sep. 9, 2011.

(51) Int. Cl.
| | | |
|---|---|---|
| *C07K 7/06* | (2006.01) | |
| *A61K 39/295* | (2006.01) | |
| *A61K 39/12* | (2006.01) | |
| *C07K 5/103* | (2006.01) | |
| *C12N 7/00* | (2006.01) | |
| *A61K 39/00* | (2006.01) | |

(52) U.S. Cl.
CPC ............... *A61K 39/295* (2013.01); *A61K 39/12* (2013.01); *C07K 5/101* (2013.01); *C07K 7/06* (2013.01); *C12N 7/00* (2013.01); *A61K 2039/523* (2013.01); *A61K 2039/542* (2013.01); *A61K 2039/552* (2013.01); *A61K 2039/55566* (2013.01); *A61K 2039/70* (2013.01); *C07K 2319/00* (2013.01); *C12N 2720/10023* (2013.01); *C12N 2720/10034* (2013.01); *C12N 2720/10044* (2013.01); *C12N 2720/12023* (2013.01); *C12N 2720/12034* (2013.01); *C12N 2760/16034* (2013.01); *C12N 2760/16043* (2013.01)

(58) Field of Classification Search
None
See application file for complete search history.

(56) References Cited

U.S. PATENT DOCUMENTS

| 5,780,448 A | 7/1998 | Davis |
|---|---|---|
| 2004/0253580 A1 | 12/2004 | Villoing et al. |
| 2005/0136071 A1 | 6/2005 | Griffiths et al. |
| 2005/0163795 A1* | 7/2005 | Simard et al. ............. 424/186.1 |
| 2008/0274126 A1 | 11/2008 | Florack et al. |
| 2009/0238845 A1 | 9/2009 | Harel |

OTHER PUBLICATIONS

Allnutt et al., Vaccine, 2007, vol. 25, pp. 4880-4888.*
Allnutt, F. C. T., et al.; *Antigenicity of Infectious Pancreatic Necrosis Virus VP2 Subviral Particles Expressed in Yeast*; Vaccine, Jun. 21, 2007, vol. 25, No. 26, pp. 4880-4888, ISSN 0264-410X; See p. 4881.
International Search Report Issued for Application No. PCT/US2012/054125 Dated Feb. 26, 2013.
International Preliminary Report on Patentability Issued for International Application No. PCT/US2012/054125 Issued on Mar. 12, 2014 and Written Opinion of the International Searching Authority Completed Feb. 25, 2013.
Bowers, R. M., et al., 2008. "Detection and quantification of infectious pancreatic necrosis virus by real-time reverse transcriptase polymerase chain reaction using lethal and non-lethal sampling," J. Virol. Methods 147, 226-234.
Chackerian, B. 2007. Virus-like particles: flexible platforms for vaccine development. Expert. Rev. Vaccines 6: 381-390.
Cotte, L. et al., "Infectious salmon anemia virus—Genetics and pathogenesis," 2010, Virus Res. 155: pp. 10-19.
Cunningham, C. O., Gregory, A., Black, J., Simpson, I., and Raynard, R. S. 2002. A novel variant of the infectious salmon anemia virus (ISAV) haemagglutinin gene suggests mechanisms for virus diversity. Bull. Eur. Assoc. Fish Pathol. 22(6): 366-374.
Dhar, A. K. et al., "Expression of a foreign epitope on infectious pancreatic necrosis virus VP2 capsid protein sub-viral particle (SVP) and immunogenicity in rainbow trout," Antiviral Res. 2010, 85: pp. 525-531.
Dobos, P. et al., "Biophysical studies of infectious pancreatic necrosis virus," 1977 J. Virol. 22: 150-159.
Duncan, R. et al., "Synthesis of the infectious pancreatic necrosis virus polyprotein, detection of a virus-encoded protease, and fine structure mapping of genome segment A coding regions," 1987, J. Virol. vol. 61, No. 12, pp. 3655-3664.

(Continued)

*Primary Examiner* — Michele K Joike
*Assistant Examiner* — Mindy G Brown
(74) *Attorney, Agent, or Firm* — RatnerPrestia

(57) ABSTRACT

The present invention provides bivalent oral vaccines against infectious pancreatic necrosis virus (IPNV) and infectious salmon anemia virus (ISAV). Yeast cells comprise an expression vector comprising (i) a polynucleotide sequence encoding a VP2 capsid protein of IPNV and (ii) a polynucleotide sequence encoding one or more antigenic epitopes of hemaglutinin of ISAV. The yeast cells express sub-viral particles (SVP) comprising a VP2 capsid protein of IPNV and one or more antigenic epitopes of hemaglutinin of ISAV. The yeast cells and SVP may be administered in an effective amount to increase the amount of antibodies against IPNV and ISAV in the fish, preferably Salmonidae. The yeast cells and SVP may be in the form of fish food for administering to the fish orally.

7 Claims, 4 Drawing Sheets

(56) References Cited

OTHER PUBLICATIONS

Falk, K. et al., "Identification and characterization of viral structural proteins of infectious salmon anemia virus," 2004, J. Virol. vol. 78, No. 6, pp. 3063-3071.

Frost P. et al., "Mapping of neutralization epitopes on infectious pancreatic necrosis viruses," J. Gen. Virol. 1995, 76, pp. 1165-1172.

Garcea, R. L. et al., "Virus-like particles as vaccines and vessels for the delivery of small molecules," 2004, Curr. Opin. Biotech. 15: 513-517.

Grgacic, E. V. L. et al., "Virus-like particles: Passport to immune recognition" 2006, Methods 40: 60-65.

Gilbert, L. et al., "Molecular and structural characterization of fluorescent human parvovirus B19 virus-like particles," 2005, Biochem Biophys Res Commun. 331: 527-535.

Gomez-Casado, E. et al., "A comparative review on European-farmed finfish RNA viruses and their vaccines," 2011, Vaccine 29: 2657-2671.

Harper, D. M. et al., "Sustained efficacy up to 4.5 years of a bivalent LI virus-like particle vaccine against human papilloma virus types 16 and 18: follow-up from a randomized control trial," 2006, Lancet 367: 1247-1255.

Heppell J. et al., "Strain variability and localization of important epitopes on the major structural protein (VP2) of infectious pancreatic necrosis virus," 1995, Virology 214: 40-49.

Hernando, E. et al., "Biochemical and physical characterization of parvovirus of minute virus of mice virus-like particles," 2000, Virology 267: 299-309.

Hou, L. et al., "Expression and self-assembly of virus-like particles of infectious hypodermal hematopoietic necrosis virus in *Escherichia coli*," 2009, Arch. Virol 154: 547-553.
Houston, R. D., et al., "Detection and confirmation of a major QTL affecting resistance to infectious pancreatic necrosis (IPN) in Atlantic salmon (*Salmo salar*)," 2008, Anim. Genomics Anim. Health 132: pp. 199-204, abstract only.
Jorgensen, S. M. et al., "Validation of reference genes for real-time polymerase chain reaction studies in Atlantic salmon," 2006, Mar. Biotechnol. 8: 398-408.
Kawaoka, Y., et al. 2005.Family Orthomyxoviridae. In: Faquet, et al. (Eds.), Virus Taxomony: Classification and nomenclature of viruses. VIIIth Report of the International Committee on Taxonomy of Viruses. Elsevier Academic Press, San Diego, CA, pp. 681-693.
Kibenge, F. S., Munir, K., Kibenge, M. J., Joseph, T., and Moneke, E. 2004. Infectious salmon anemia virus: Casautive agent, pathogenesis and immunity. Anim. Health Res. Rev. 5: 65-78.
Kibenge, F. S., Kibenge, M. J., Wang, Y., Qian, B., Hariharan, S., and McGeachy, S. 2007. Mapping of putative virulence motifs on infectious salmon anemia virus surface glycoprotein gens. J. Gen. Virol. 88: 3100-3111.
Krossoy, B. et al., "Cloning and characterization of the infectious salmon anemia virus haemagglutinin," 2001, J. Gen. Virol. 82: 1757-1765.
Labus, M. B. et al., "Antigenic comparison of a truncated form of VP2 of infectious pancreatic necrosis (IPN) virus expressed in four different cell types," 2001, Fish & Shellfish Immunol. 11: 203-216.
Landry, N.et al., "Preclinical and clinical development of plant-made virus-like particle vaccine against avian H5N1 influenza," 2010, PLoS One 5(12): el5559.
Lauscher, A. et al., "Immune response in Atlantic salmon (*Salmo salar*) following protective vaccination against infectious salmon anemia (ISAV) and subsequent ISA virus infection," 2011, Vaccine 29, pp. 6392-6401.
Magyar, G, et al., "Evidence to the detection of the infectious pancreatic necrosis virus polyprotein and the 17 kDa polypeptide in infected cells and the NS protease in purified virus," 1994, Virology 204: 580-589.
Mao, C. et al., "Efficacy of human papilloma virus-16 vaccine to prevent cervical intraepithelian neoplasia: a randomized control trial," 2006, Obstet. Gynecol. vol. 107, No. 1, 18-27pp.
Mjaaland, S., et la., "Polymorphism in the infectious salmon anemia virus haemagglutinin gene: importance and possible implications for evolution and ecology of infectious salmon anemia disease," 2002, Virology 304: 379-391.
Muller, A. et al., "Structural and functional analysis of the hemagglutinin-esterase of infectious salmon anemia virus," 2010, Virus Res. 151: 131-141.
Ozaki, A. et al., "Quantitative trait loci (QTLs) associated with resistance/susceptibility to infectious pancreatic necrosis virus (IPNV) in rainbow trout (*Oncorhynchus mykiss*)," 2001, Mol. Gen. Genet. 265:23-31.
Pannunzio, V.G. et al., "Yeast Plasmids with the Least Trouble," 2004, Promega Notes 87: 27-28.
Pederson, T. et al., "VP3, a structural protein of infectious pancreatic necrosis virus, interacts with RNA-dependent RNA polymerase VP1 and with double-stranded RNA," 2007, J. Virol. vol. 81, No. 12, pp. 6652-6663.
Pous, J. et al., "Structure of bimavirus-like particles determined by combined electron cryomicroscopy and X-ray crystallography," 2005, J. Gen. Virol. 86: 2339-2346.
Ramanos, M.A. et al., "Foreign gene expression in yeast: a review," 1992, Yeast 8: 423-488.
Raynard, R. S. et al., "Experimental infection model and susceptibility of Atlantic salmon (*Salmo salar*) to a Scotish isolate of infectious salmon anemia virus (ISAV)," 2001, Dis Aquat Org.47: 169-174.
Remond, M. et al., "Infectious bursal disease subviral particles displaying the foot-and-mouth disease virus major antigenic site," 2009, Vaccine 27: 93-98.
Rimstad, E. et al., "Characterization of the infectious salmon anemia virus genome segment that encodes the putative haemagglutinin," 2001, J. Virol. vol. 75, No. 11, pp. 5352-5356.
Santi, N. et al., "Identification of putative motifs involved in the virulence of infectious pancreatic necrosis virus," 2004, Virology 322: 31-40.
Sedlik, C et al., "Recombinant parvovirus-like particles as an antigen carrier: a novel non-replicative exogenous antigen to elicit protective antiviral cytotoxic T cells," 1997, Proc. Natl. Acad. Sci. USA 94: 7503-7508.
Shivappa, R. B. et al., "Development of a subunit vaccine for infectious pancreatic necrosis virus using a baculovirus insect/larvae system. In: P. J. Midtlyng (ed.) Progress in Fish Vaccinology," 2005, Dev. Biol. Basel 121: 165-174, abstract only.
Sundh, H. et al., "The effect of hyperoxygenation and reduced flow in fresh water and subsequent infectious pancreatic necrosis virus challenge in sea water, on the barrier integrity in Atlantic salmon (*Salmo salar*)," 2009, J. Fish Dis. 32: 687-698.
Thorud, K. E. et al., "Infectious salmon anaemia in Atlantic salmon (*Salmo salar*)," 1988, Bull. Eur. Assoc. Fish Pathol. 8: 109-111.
Tobar, J. A. et al., "Oral vaccination against infectious salmon anemia in atlantic salmon (*Salmo salar*) induces specific immunity and provides protection against infectious salmon anemia virus challenge," 2010, World Aquaculture Society Meeting, San Diego, CA.
Tobar, J. A. et al., "Oral vaccination of Atlantic salmon (*Salmo salar*) against salmonid rickettsial septicaemia," 2011, Vaccine 29: 2336-2340.
Workenhe. S. T. et al., "Absolute quantitation of infectious salmon anaemia virus using different real-time reverse transcription PCR chemistries," 2008, J Virol Methods. 154:128-34.
European Search Report for European Application No. 12830040.7 dated May 7, 2015.
Dhar, A. K. et al,. "Viral vaccines for farmed finfish," VirusDisease, vol. 25, No. 1, Jan.-Mar. 2014, pp. 1-17.
Wolf, A. et al., "A hemagglutinin-esterase-expressing salmonid alphavirus replicon protects Atlantic salmon (*Salmo salar*) against infectious salmon anemia (ISA)," Vaccine, vol. 31, No. 4, 2013, pp. 661-669.

* cited by examiner

Figure 2B

*Plasmid map: pIPNV/ISAV-rVP2-E1-252*

Labels: 2-micron origin, yeast URA3 ORF, f1 origin, ADH1 terminator, Site 252, E1/E2/E3, rVP2, GAL1/GAl10 divergent promoter, MCS, CYC1 terminator, pUC origin, AmpR

Figure 2C

*Plasmid map: pIPNV/ISAV-rVP2-E1-286*

Labels: 2-micron origin, yeast URA3 ORF, f1 origin, ADH1 terminator, Site 286, E1/E2/E3, VP2, GAL1/GAl10 divergent promoter, MCS, CYC1 terminator, pUC origin, AmpR ically necrosis in salmonids fish. These VLPs contained both structural proteins, VP2 and VP3, of IPNV, and are similar in size compared to the native virus (McKenna et 5 al., 2001; Shivappa et al., 2005).
IPNV-ISAV BIVALENT VACCINE USING A VIRUS-LIKE PARTICLE-BASED PLATFORM AND METHODS OF USING THE SAME

CROSS-REFERENCE TO RELATED APPLICATIONS

This application is a national phase application of International Application No. PCT/US2012/054125, filed Sep. 7, 2012, which claims priority to U.S. Application No. 61/533, 020, filed Sep. 9, 2011, which applications are incorporated by reference herein in their entireties and for all purposes.

FIELD OF THE INVENTION

This invention relates generally to vaccines against infectious pancreatic necrosis virus (IPNV) and infectious salmon anemia virus (ISAV) in fish. More specifically, the invention relates to a bivalent vaccine comprising subvirus-like particles (SVP) that comprise antigenic epitopes of IPNV and ISAV.

BACKGROUND OF THE INVENTION

The intrinsic ability of structural protein(s) of many viruses to self-assemble into virus-like particles (VLPs) has led to the development of a specific class of subunit vaccine (Chackerian, 2007; Grgacic and Anderson, 2006; Garcea and Gissmann, 2004). VLPs are generally similar to viruses in shape, size and morphology but are non-infectious due to the lack of infectious component of a virus. VLPs are highly immunogenic and the cellular uptake and the intracellular trafficking of VLPs are similar to viruses (Grgacic and Anderson, 2006). Thus, VLPs combine the advantages of both whole virus as well as subunit vaccines (Chackerian, 2007; Ludwig and Wagner, 2007). VLPs have been expressed using a variety of expression system including bacteria, yeast, transgenic plant, insect and mammalian cell culture systems and against a wide array of viruses infecting human, animals and plants. For example, VLPs made from hepatitis B virus (HBV) major surface antigen are commercially available as Recombivax® (Merck & Co, Inc.) and Energix (GlaxoSmithKline [GSK], Inc.). VLPs assembled from human papillomavirus (HPV) major capsid protein, LI in yeast was approved as a vaccine (Gardasil®, Merck) against cervical cancer in human. A competing product, named Cervarix™ (GSK), made using a baculovirus expression system in insect cell culture was approved in 2006. Both these vaccines elicited a stable antibody response and a long-term protection against infection with cognate virus (Mao et al., 2006; Harper et al., 2006).

VLPs have also been made against many other human viruses such as, Norwalk virus, rotavirus, influenza virus, SARS coronavirus, Ebola virus, and poliovirus (reviewed by Grgacic and Anderson, 2006; Landry et al., 2010). Efforts have also been made to use VLPs as candidate for developing vaccine against animal viruses such as infectious bursal disease of poultry (Remond et al., 2009); canine parvovirus (Gilbert et al., 2004); parvovirus of mice (Hernando et al., 2000); and porcine parvovirus (Sedlik et al, 1999).

In recent years, efforts have been made to develop VLP-based vaccine in shellfish and fish. For example, the capsid protein of infectious hypodermal and hematopoietic necrosis virus, a parvovirus that infects penaeid shrimp (*Penaeus* sp.), when expressed in *Escherichia coli*, was found to self-assemble into VLPs that are similar in size and shape to cognate virus and are taken up by the hemocytes in primary culture. This opened up a possibility of using VLPs as vehicles for delivery of antiviral therapies in shrimp (Hou et al., 2009). VLPs have been expressed in mammalian cells (hamster fibroblast cells, BHK-21, McKenna et al., 2001) and in insect larvae (*Tricopiusui ni*, Shivappa et al., 2005) for an infectious pancreatic necrosis virus (IPNV) that causes infectious pancreatic necrosis in salmonids fish. These VLPs contained both structural proteins, VP2 and VP3, of IPNV, and are similar in size compared to the native virus (McKenna et 5 al., 2001; Shivappa et al., 2005).

More recently, Allnutt and colleagues expressed one of the two capsid proteins, VP2, of IPNV in yeast that self-assembled to sub-viral particles (SVP) (Allnutt et al., 2007). The IPNV SVPs were 22 nm in size compared to the 60 nm size of the VLPs expressed in mammalian cells and in insect larvae. Since most of the antigenic epitopes of IPNV are located in VP2 protein, the yeast expressed IPNV SVP when injected or orally administered into rainbow trout elicited antibody response. In addition, vaccinated fish when challenged with a cognate infectious virus, showed significant reduction in viral load compared to the unvaccinated fish (Allnutt et al., 2007). This showed the potential of using IPNV SVP as a candidate for developing injectable as well as oral vaccine.

Subsequently, to evaluate the potential of IPNV VP2 SVP as a platform to produce bivalent vaccine, a heterologous epitope, human oncogene epitope c-myc, was cloned into IPNV SVP backbone and expressed in yeast. The chimeric VLP when injected into rainbow trout elicited antibody response not only against IPNV but also against the c-myc epitope (Dhar et al., 2010). When fish vaccinated with chimeric VLPs were injected with IPNV, vaccinated fish had a significant reduction in viral load compared to unvaccinated fish. This indicated that IPNV VLP can tolerate the insertion of foreign epitope without affecting the antigenicity of the backbone peptide or the foreign epitope (Dhar et al., 2010). This opened up a possibility of using IPNV VLP as a platform to developing a bivalent vaccine against major viral diseases in salmonids fish.

Infectious pancreatic necrosis (IPN) caused by IPNV and infectious salmon anemia (USA) caused by the infectious salmon anemia virus (ISAV) are the two major viral diseases in salmonid. IPNV is a bi-segmented double-stranded RNA (dsRNA) containing virus belonging to the family Birnaviridae, genus *Aquabirnavims*. Segment B of the viral genome encodes a RNA-dependent-RNA-polymerase protein, VP1. Segment A encodes a polyprotein which is co-translationally cleaved by the viral-encoded serine-lysine protease, VP4 to make capsid proteins, precursor VP2 (pVP2) and VPS (Duncan et al., 1987; Dobos et al., 1997). Subsequently pVP2 is processed by the host cell protease to form mature VP2 capsid protein (Magyar and Dobos, 1994). VP2 constitutes the outer shell of the viral capsid proteins (Pous et al., 2005). It is quite abundant and contains most of the antibody neutralizing epitopes (Frost et al., 1995; Heppell et al., 1995). Amino acid residues 217 and 221 in the VP2 protein are the major determinants of virulence in IPNV (Santi et al., 2004). VPS, on the other hand, constitutes the inner structural protein and remain bound to viral genomic dsRNA to form the ribonucleoprotein core structure (Pederson et al., 2007). VPS also binds to RdRp protein, VP1. It has been reported that VPS carries some antigenic epitopes. In addition to the capsid protein open reading frame (ORF), Segment A also encodes a small arginine-rich non-structural protein VPS, the biological functions of which is unknown.

Infectious pancreatic necrosis (IPN) is an important disease of finfish worldwide. The disease causes high mortality in fry and post-smolt salmon. In recent years, a number of vaccines against IPN have been commercialized (reviewed by Gomez-Casado et al., 2011). These include Alpha Ject® 1000 (licensed in Norway, Chile and UK, Pharmaq AS, Norway), Bimagen Forte (licensed in Canada, Aqua Health Ltd., Novartis, Canada), IPNV (licensed in Chile, CENTROVET, Chile), Norvax (Intervet-International BV, The Netherlands), and SRS/IPNV/Vibrio (licensed in Canada and Chile, Microtek International Inc., British Columbia, Canada). The first three of these vaccines are composed of inactivated virus while the remaining two contain recombinant VP2. However, the modes of delivery for all of these vaccines are via intraperitoneal injection route. Despite a vaccination program implemented by fish farmers, outbreaks of IPN disease occur from time to time and mortality rates during outbreak vary depending on the genetic susceptibility of the stock, environmental stress and viral strains (Ozaki et al., 2001; Houston et al., 2008; Sundh et al, 2009).

Infectious salmon anemia (USA) was first reported in Atlantic salmon (*Salmo salar*) from Norway in 1984 (Thorud and Djupvik, 1988). Since then the disease has been reported in Atlantic salmon from Canada, USA and Scotland and Coho salmon (*Oncorhynchus kisutch*) in Chile (reviewed by Cotte et al., 2010; Gomez-Casado et al., 2011). The cumulative mortality due to ISA outbreak can reach up to 100% (Kibenge et al., 2004). ISAV is an enveloped virus containing eight negative-sense single-stranded linear RNA segments and belongs to the family Orthomyxoviridae, genus *Isavirus* (Kawaoka et al, 2005). It has been reported that in ISAV the virulence lies mainly in the viral encoded proteins hemagglutinin esterase (HE) and fusion glycoproteins (Kibenge et al, 2007; Muller et al, 2010; Cotte et al, 2010). A number of vaccines have been commercialized against ISA. These include Alpha Jects® and Micro-1 ISA (licensed in Norway, Ireland, Finland and Chile, Pharmaq AS, Norway), FORTE VI (Licensed in Canada, Aqua Health Ltd., Novartis, Canada), ISA vaccine (licensed in Canada, Microtek International, British Columbia, Canada), and ISAV (CENTROVET Ltda., Chile). All but CENTROVET ISAV vaccines are composed of inactivated whole ISAV, and are delivered via injection route. ISAV vaccine of CENTROVET Ltda., on the other hand, contains recombinant HE protein expressed in yeast and is delivered via oral route (Tobar et al., 2010).

As fish farming is expanding globally, vaccinations are playing an increasingly important role in fish health management. An ideal viral vaccine must induce long lasting protection at an early age, prevent carrier formation, and be effective against a large number viral serotypes. Injection cannot be used for small fish; therefore, either oral delivery or immersion are more preferred routes for early vaccination. These attributes of a vaccine must be met either by a recombinant subunit vaccine or by an inactivated viral vaccine, as a live attenuated vaccine could potentially lead to carrier formation.

SUMMARY OF THE INVENTION

An embodiment of the present invention provides an expression vector comprising polynucleotide sequences encoding antigenic epitopes of infectious pancreatic necrosis virus (IPNV) and infectious salmon anemia virus (ISAV). In preferred embodiments, the expression vector comprises (i) a polynucleotide sequence encoding a VP2 capsid protein of infectious pancreatic necrosis virus (IPNV) and (ii) a polynucleotide sequence encoding one or more antigenic epitopes of infectious salmon anemia virus (ISAV) (e.g., one or more epitopes of hemaglutinin). The expression vector is preferably suitable for expression in yeast cells.

Another embodiment of the present invention provides a yeast cell or yeast cells comprising an expression vector comprising polynucleotide sequences encoding antigenic epitopes of infectious pancreatic necrosis virus (IPNV) and infectious salmon anemia virus (ISAV). In preferred embodiments, the expression vector comprises (i) a polynucleotide sequence encoding a VP2 capsid protein of IPNV and (ii) a polynucleotide sequence encoding one or more antigenic epitopes of ISAV (e.g., one or more epitopes of hemaglutinin). The yeast cells preferably express sub-viral particles (SVP) comprising a VP2 capsid protein of IPNV and one or more antigenic epitopes of ISAV (e.g., one or more epitopes of hemaglutinin). In preferred embodiments, the polynucleotide sequence encoding the one or more epitopes of hemagglutinin of ISAV is located within (i.e., is inserted within) the polynucleotide sequence encoding the VP2 capsid protein. For example, the polynucleotide sequence encoding the one or more epitopes of hemagglutinin of ISAV is located at either (i) the nucleotide position 756 in the polynucleotide sequence encoding the VP2 capsid protein, wherein the nucleotide position 756 corresponds to amino acid position 252 of the VP2 capsid protein; or (ii) the nucleotide position 858 in the polynucleotide sequence encoding the VP2 capsid protein, wherein the nucleotide position 858 corresponds to amino acid position 286 of the VP2 capsid protein.

Another embodiment of the present invention provides yeast cells comprising an expression vector comprising (i) a polynucleotide sequence encoding a VP2 capsid protein of IPNV and (ii) a polynucleotide sequence encoding one or more epitopes of hemaglutinin of ISAV, wherein the polynucleotide sequence encoding the one or more epitopes of hemaglutinin encodes one or more amino acid sequences selected from the group consisting of: LLAPVYSR (SEQ ID NO: 7), RGDVRVTP (SEQ ID NO: 8), NKCV (SEQ ID NO: 9), FSVKVLTF (SEQ ID NO: 10), IYKVCIA (SEQ ID. NO: 11), FGIALFL (SEQ ID NO: 12), and a combination thereof.

Another embodiment of the present invention provides yeast cells comprising an expression vector comprising (i) a polynucleotide sequence encoding a VP2 capsid protein of IPNV and (ii) a polynucleotide sequence encoding one or more epitopes of hemaglutinin of ISAV, wherein the one or more epitopes of hemaglutinin are selected from the group consisting of: CTGTTGGCGCCTGTTTACAGTCGC (SEQ ID NO: 1), AGGGGAGACGTGAGAGTGACGCCT (SEQ ID NO: 2), AACAAGTGTGTT (SEQ ID NO: 3), TTTTCG-GTGAAGGTGTTGACTTTC (SEQ ID NO: 4), ATCTA-CAAGGTCTGCATTGCA (SEQ ID NO: 5), TTTGGGAT-TGCTCTGTTCCTA (SEQ ID NO: 6), and a combination thereof.

Another embodiment of the present invention provides a fish food comprising yeast cells in accordance with the present invention. In preferred embodiments, the fish food further comprises sub-viral particles (SVP) expressed by the yeast cells in accordance with the present invention.

Another embodiment of the present invention provides an oral fish vaccine comprising yeast cells in accordance with the present invention. In preferred embodiments, the oral fish vaccine further comprises sub-viral particles (SVP) expressed by the yeast cells in accordance with the present invention.

Another embodiment of the present invention provides an injectable fish vaccine comprising yeast cells in accordance with the present invention. In preferred embodiments, the injectable fish vaccine further comprises sub-viral particles (SVP) expressed by the yeast cells in accordance with the present invention.

Another embodiment of the present invention provides sub-viral particles (SVP) comprising a VP2 capsid protein of IPNV and one or more epitopes of hemaglutinin of ISAV. In preferred embodiments, the one or more epitopes of hemaglutinin comprise one or more amino acid sequences selected from the group consisting of: LLAPVYSR (SEQ ID NO: 7), RGDVRVTP (SEQ ID NO: 8), NKCV (SEQ ID NO: 9), FSVKVLTF (SEQ ID NO: 10), IYKVCIA (SEQ ID. NO: 11), and FGIALFL (SEQ ID NO: 12).

Another embodiment of the present invention provides a method for vaccinating fish against IPNV and ISAV (e.g., for increasing immunity of the fish, or antibody titers in the fish, against IPNV and ISAV) comprising administering yeast cells to the fish, wherein the yeast cells comprise an expression vector comprising (i) a polynucleotide sequence encoding a VP2 capsid protein of IPNV and (ii) a polynucleotide sequence encoding one or more epitopes of hemagglutinin of ISAV. The yeast cells may be administered to the fish orally or via injection. The fish are preferably of the family Salmonidae (e.g., salmon or trout).

Another embodiment of the present invention provides a method for vaccinating fish against IPNV and ISAV comprising administering an effective amount of the yeast cells in accordance with the present invention to increase the amount of antibodies (e.g., antibody titer) against IPNV and ISAV in the fish compared to fish that have not been administered the yeast cells. Another embodiment of the present invention provides a method for vaccinating fish against IPNV and ISAV comprising administering an effective amount of the yeast cells in accordance with the present invention to increase the amount of antibodies (e.g., antibody titer) against IPNV in the fish compared to fish that have been administered yeast cells that express only the VP2 capsid protein (i.e., yeast cells that do not also express SVPs having an epitope of ISAV).

Another embodiment of the present invention provides a method of making sub-viral particles (SVP) comprising a VP2 capsid protein of IPNV and one or more epitopes of hemaglutinin of ISAV comprising transforming yeast cells with an expression vector comprising (i) a polynucleotide sequence encoding a VP2 capsid protein of IPNV and (ii) a polynucleotide sequence encoding one or more epitopes of hemaglutinin of ISAV. In preferred embodiments, the method further comprises maintaining suitable conditions for the yeast cells to express sub-viral particles comprising the VP2 capsid protein of IPNV and the one or more epitopes of hemaglutinin of ISAV.

BRIEF DESCRIPTION OF THE FIGURES

The invention may be further understood by reference to the following drawings.

DETAILED DESCRIPTION OF THE INVENTION

Figure 1:
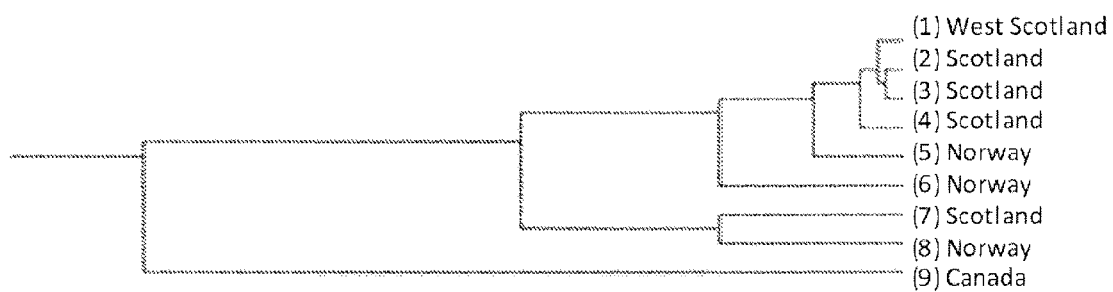
FIG. 1 illustrates a neighbor-joining tree using the UPGMA clustering based on the full-length predicted amino acid sequence of hemaglutinin (HA) gene of infectious salmon anemia virus (ISAV). The GenBank accession numbers of the HA sequences used in the phylogenetic analysis are given: (1) W. Scotland (AJ276859.1), (2) Scotland (AF388582.1), (3) Scotland (AF283997.2), (4) Scotland (AF388581.1), (5) Norway (AF378180.2), (6) Norway (AF378181.2), (7) Scotland (AF391126.1), (8) Norway (AF220607.1), and (9) Canada (AF294881.2).

The applicant has discovered that virus-like particle (VLP) expressed in yeast is an attractive platform technology for developing a vaccine against both IPN and ISA in salmonids. A capsid protein, VP2, of infectious pancreatic necrosis virus (IPNV) aggregates to form VLP when expressed in yeast. As used herein, a "subvirus-like particle" (used interchangeably herein with the term "sub-virus particle"), is a virus-like particle (VLP) that is smaller than the size of the native virus. Since IPNV capsid proteins contain two different proteins, VP2 and VP3, and the VLP formed by the VP2 protein alone is smaller than the size of the native virus, it is called a subvirus-like particle (SVP).

In accordance with embodiments of the present invention, antigenic epitopes of infectious salmon anemia virus (ISAV) were cloned into the backbone of sub-viral particles (SVP) representing VP2 capsid protein of infectious pancreatic necrosis virus (IPNV). The chimeric SVP was expressed in yeast. In particular embodiments, recombinant yeast expressing chimeric SVP were encapsulated using Advanced BioNutrition (ABN) Corporation MicroMatrix® technology and top coated onto feed before vaccinating rainbow trout via oral route. In vaccinated fish, antibodies were detected not only against the IPNV but also against ISAV HA epitope at 30 and 60 days post-vaccination. It was also unexpectedly discovered that the addition of ISAV epitope into the IPNV SVP backbone increased the antibody titer against the IPNV backbone compared to fish vaccinated with only IPNV SVP. The data showed that the IPNV SVP tolerate the insertion of ISAV HA epitopes without affecting the antigenicity of IPNV as well as ISAV HA epitopes. Therefore, yeast expressed IPNV/ISAV chimeric VLP may be used as a bivalent vaccine against infectious pancreatic necrosis (IPN) and infectious salmon anemia (ISA) diseases in salmonids fish.

Yeast was chosen as the preferred expression platform for a variety of reasons. The yeast expression system has a potential value for oral vaccine development, since yeast is already a component of fish feeds and is generally regarded as safe. This contrasts with bacterial expression in *Escherichia coli*, which generates pyrogens that would need to be removed before use of any crude preparation as an oral vaccine (Ramanos et al., 1992). The use of yeast is also attractive because production is economical and, through well-developed genetic systems, can be engineered to provide an abundant supply of the protein or proteins of interest. The ease of scale up with the production of yeast contrasts with fish and insect cell culture that have a high cost of production. In addition, the expressed proteins are post-translationally modified by the addition of sugar groups that could make the expressed protein more immunogenic.

An embodiment of the present invention provides an expression vector comprising polynucleotide sequences encoding antigenic epitopes of infectious pancreatic necrosis virus (IPNV) and infectious salmon anemia virus (ISAV). In preferred embodiments, the expression vector comprises (i) a polynucleotide sequence encoding a VP2 capsid protein of infectious pancreatic necrosis virus (IPNV) and (ii) a polynucleotide sequence encoding one or more antigenic epitopes of infectious salmon anemia virus (ISAV) (e.g., one or more epitopes of hemaglutinin). The expression vector is preferably suitable for expression in yeast cells.

Another embodiment of the present invention provides a yeast cell or yeast cells comprising an expression vector comprising polynucleotide sequences encoding antigenic epitopes of infectious pancreatic necrosis virus (IPNV) and infectious salmon anemia virus (ISAV). As used herein, "yeast cells" comprising an expression vector of the present invention refers to either all of the yeast cells, substantially all of the yeast cells, or some of the yeast cells (e.g., one or more of the yeast cells) comprising an expression vector of the present invention. In preferred embodiments, the expression vector comprises (i) a polynucleotide sequence encoding a VP2 capsid protein of IPNV and (ii) a polynucleotide sequence encoding one or more antigenic epitopes of ISAV (e.g., one or more epitopes of hemaglutinin). The yeast cells preferably express sub-viral particles (SVP) comprising a VP2 capsid protein of IPNV and one or more antigenic epitopes of ISAV (e.g., one or more epitopes of hemaglutinin).

Another embodiment of the present invention provides yeast cells comprising an expression vector comprising (i) a polynucleotide sequence encoding a VP2 capsid protein of IPNV and (ii) a polynucleotide sequence encoding one or more epitopes of hemaglutinin of ISAV, wherein the polynucleotide sequence encoding the one or more epitopes of hemagglutinin of ISAV is located within (i.e., is inserted within) the polynucleotide sequence encoding the VP2 capsid protein. In preferred embodiments, the polynucleotide sequence encoding the one or more epitopes of hemagglutinin of ISAV is located at either (i) the nucleotide position 756 in the polynucleotide sequence encoding the VP2 capsid protein, wherein the nucleotide position 756 corresponds to amino acid position 252 of the VP2 capsid protein; or (ii) the nucleotide position 858 in the polynucleotide sequence encoding the VP2 capsid protein, wherein the nucleotide position 858 corresponds to amino acid position 286 of the VP2 capsid protein.

Another embodiment of the present invention provides yeast cells comprising an expression vector comprising (i) a polynucleotide sequence encoding a VP2 capsid protein of IPNV and (ii) a polynucleotide sequence encoding one or more epitopes of hemaglutinin of ISAV, wherein the polynucleotide sequence encoding the one or more epitopes of hemaglutinin encodes one or more amino acid sequences selected from the group consisting of: LLAPVYSR (SEQ ID NO: 7), RGDVRVTP (SEQ ID NO: 8), NKCV (SEQ ID NO: 9), FSVKVLTF (SEQ ID NO: 10), IYKVCIA (SEQ ID. NO: 11), FGIALFL (SEQ ID NO: 12), and a combination thereof. According to a particular embodiment, the polynucleotide sequence encoding the one or more epitopes of hemaglutinin encodes one or more amino acid sequences selected from the group consisting of: LLAPVYSR (SEQ ID NO: 7), RGDVRVTP (SEQ ID NO: 8), NKCV (SEQ ID NO: 9), and a combination thereof. For example, the polynucleotide sequence encoding the one or more epitopes of hemaglutinin may encode a combination of the following three amino acid sequences: LLAPVYSR (SEQ ID NO: 7), RGDVRVTP (SEQ ID NO: 8), and NKCV (SEQ ID NO: 9).

Another embodiment of the present invention provides yeast cells comprising an expression vector comprising (i) a polynucleotide sequence encoding a VP2 capsid protein of IPNV and (ii) a polynucleotide sequence encoding one or more epitopes of hemaglutinin of ISAV, wherein the polynucleotide sequence encoding the one or more epitopes of hemaglutinin of ISAV is selected from the group consisting of: CTGTTGGCGCCTGTTTACAGTCGC (SEQ ID NO: 1), AGGGGAGACGTGAGAGTGACGCCT (SEQ ID NO: 2), AACAAGTGTGTT (SEQ ID NO: 3), TTTTCGGTGAAGGTGTTGACTTTC (SEQ ID NO: 4), ATCTACAAGGTCTGCATTGCA (SEQ ID NO: 5), TTTGGGATTGCTCTGTTCCTA (SEQ ID NO: 6), and a combination thereof. According to preferred embodiments, the polynucleotide sequence encoding the one or more epitopes of hemaglutinin is selected from the group consisting of: CTGTTGGCGCCTGTTTACAGTCGC (SEQ ID NO: 1), AGGGGAGACGTGAGAGTGACGCCT (SEQ ID NO: 2), AACAAGTGTGTT (SEQ ID NO: 3), and a combination thereof. For example, the polynucleotide sequence encoding the one or more epitopes of hemaglutinin may comprise a combination of the following three sequences: CTGTTGGCGCCTGTTTACAGTCGC (SEQ ID NO: 1), AGGGGAGACGTGAGAGTGACGCCT (SEQ ID NO: 2), and AACAAGTGTGTT (SEQ ID NO: 3). The polynucleotide sequence encoding the one or more epitopes of hemaglutinin may alternatively comprise SEQ ID NO: 1, SEQ ID NO: 2, SEQ ID NO: 3, SEQ ID NO: 4, SEQ ID NO: 5, SEQ ID NO: 6, or a combination thereof, which have one or more silent mutations, i.e., the DNA sequence has one or more mutations that do not result in a change to the amino acid sequence of the resulting amino acid sequences of the one or more epitopes of hemaglutinin (e.g., that do not result in a change to SEQ ID NO: 7, SEQ ID NO: 8, SEQ ID NO: 9, SEQ ID NO: 10, SEQ ID NO: 11, SEQ ID NO: 12, or a combination thereof).

Another embodiment of the present invention provides yeast cells comprising an expression vector comprising (i) a polynucleotide sequence encoding a VP2 capsid protein of IPNV and (ii) a polynucleotide sequence encoding one or more epitopes of hemaglutinin of ISAV, wherein the yeast cells express sub-viral particles (SVP) comprising a VP2 capsid protein of IPNV and one or more epitopes of hemaglutinin of ISAV.

Another embodiment of the present invention provides yeast cells comprising an expression vector comprising (i) a polynucleotide sequence encoding a VP2 capsid protein of IPNV and (ii) a polynucleotide sequence encoding one or more epitopes of hemaglutinin of ISAV, wherein the yeast cells are fully or partially encapsulated by one or more excipients that are effective to enhance the stability of the yeast cells (e.g., the yeast cells may be fully or partially encapsulated by using MicroMatrix® technology).

Another embodiment of the present invention provides a fish food comprising yeast cells, wherein the yeast cells comprise an expression vector comprising (i) a polynucleotide sequence encoding a VP2 capsid protein of IPNV and (ii) a polynucleotide sequence encoding one or more epitopes of hemaglutinin of ISAV. In preferred embodiments, the yeast cells are fully or partially encapsulated by one or more excipients that are effective to enhance the stability of the yeast cells (e.g., the yeast cells may be fully or partially encapsulated by using MicroMatrix® technology).

Another embodiment of the present invention provides a fish food comprising yeast cells, wherein the yeast cells comprise an expression vector comprising (i) a polynucleotide sequence encoding a VP2 capsid protein of IPNV and (ii) a polynucleotide sequence encoding one or more epitopes of hemaglutinin of ISAV; and sub-viral particles (SVP)

expressed by the yeast cells, wherein the SVP comprise a VP2 capsid protein of IPNV and one or more epitopes of hemaglutinin of ISAV.

Another embodiment of the present invention provides an oral fish vaccine comprising yeast cells, wherein the yeast cells comprise an expression vector comprising (i) a polynucleotide sequence encoding a VP2 capsid protein of IPNV and (ii) a polynucleotide sequence encoding one or more epitopes of hemaglutinin of ISAV. In preferred embodiments, the yeast cells are fully or partially encapsulated by one or more excipients that are effective to enhance the stability of the yeast cells (e.g., the yeast cells may be fully or partially encapsulated by using MicroMatrix® technology).

Another embodiment of the present invention provides an oral fish vaccine comprising yeast cells, wherein the yeast cells comprise an expression vector comprising (i) a polynucleotide sequence encoding a VP2 capsid protein of IPNV and (ii) a polynucleotide sequence encoding one or more epitopes of hemaglutinin of ISAV; and sub-viral particles (SVP) expressed by the yeast cells, wherein the SVP comprise a VP2 capsid protein of IPNV and one or more epitopes of hemaglutinin of ISAV.

Another embodiment of the present invention provides an injectable fish vaccine comprising yeast cells, wherein the yeast cells comprise an expression vector comprising (i) a polynucleotide sequence encoding a VP2 capsid protein of IPNV and (ii) a polynucleotide sequence encoding one or more epitopes of hemaglutinin of ISAV. In preferred embodiments, the injectable fish vaccine further comprises sub-viral particles (SVP) expressed by the yeast cells, wherein the SVP comprise a VP2 capsid protein of IPNV and one or more epitopes of hemaglutinin of ISAV.

Another embodiment of the present invention provides sub-viral particles (SVP) comprising a VP2 capsid protein of IPNV and one or more epitopes of hemaglutinin of ISAV. In preferred embodiments, the one or more epitopes of hemaglutinin comprise one or more amino acid sequences selected from the group consisting of: LLAPVYSR (SEQ ID NO: 7), RGDVRVTP (SEQ ID NO: 8), NKCV (SEQ ID NO: 9), FSVKVLTF (SEQ ID NO: 10), IYKVCIA (SEQ ID. NO: 11), and FGIALFL (SEQ ID NO: 12).

Another embodiment of the present invention provides sub-viral particles (SVP) comprising a VP2 capsid protein of IPNV and one or more epitopes of hemaglutinin of ISAV, wherein the amino acid sequence encoding the one or more epitopes of hemagglutinin of ISAV is located within the amino acid sequence encoding the VP2 capsid protein (e.g., the amino acid sequence encoding the one or more epitopes of hemagglutinin of ISAV is located within the backbone of sub-viral particles comprising a VP2 capsid protein of IPNV). In preferred embodiments, the amino acid sequence encoding the one or more epitopes of hemagglutinin is located at either amino acid position 252 or 286 of the VP2 capsid protein.

Another embodiment of the present invention provides an oral fish vaccine comprising sub-viral particles which comprise a VP2 capsid protein of IPNV and one or more epitopes of hemaglutinin of ISAV. Another embodiment of the present invention provides an injectable fish vaccine comprising sub-viral particles which comprise a VP2 capsid protein of IPNV and one or more epitopes of hemaglutinin of ISAV. Another embodiment of the present invention provides a fish food comprising sub-viral particles which comprise a VP2 capsid protein of IPNV and one or more epitopes of hemaglutinin of ISAV.

Embodiments of the fish foods, oral fish vaccines, and injectable fish vaccines described herein may further comprise one or more additional excipients. For example, yeast cells and/or sub-viral particles may be encapsulated fully or partially by one or more excipients that are effective to enhance the stability and/or delivery efficiency of the yeast cells and/or sub-viral particles to the target site of action, when compared to yeast cells and/or sub-viral particles that do not comprise the same excipient(s). The MicroMatrix® technology described herein is one example of such an excipient.

Another embodiment of the present invention provides a method for vaccinating fish against IPNV and ISAV (e.g., for increasing immunity of the fish, or antibody titers in the fish, against IPNV and ISAV) comprising administering yeast cells to the fish, wherein the yeast cells comprise an expression vector comprising (i) a polynucleotide sequence encoding a VP2 capsid protein of IPNV and (ii) a polynucleotide sequence encoding one or more epitopes of hemagglutinin of ISAV. In particular embodiments, the yeast cells are administered to the fish either orally or via injection. The fish are preferably of the family Salmonidae (e.g., salmon or trout).

Another embodiment of the present invention provides a method for vaccinating fish against IPNV and ISAV comprising administering an effective amount of the yeast cells in accordance with the present invention to increase the amount of antibodies (e.g., antibody titer) against IPNV and ISAV in the fish compared to fish that have not been administered the yeast cells. Another embodiment of the present invention provides a method for vaccinating fish against IPNV and ISAV comprising administering an effective amount of the yeast cells in accordance with the present invention to increase the amount of antibodies (e.g., antibody titer) against IPNV in the fish compared to fish that have been administered yeast cells that express only the VP2 capsid protein (i.e., yeast cells that do not also express SVPs having an epitope of ISAV).

Another embodiment of the present invention provides a method of making sub-viral particles (SVP) comprising a VP2 capsid protein of IPNV and one or more epitopes of hemaglutinin of ISAV comprising transforming yeast cells with an expression vector comprising (i) a polynucleotide sequence encoding a VP2 capsid protein of IPNV and (ii) a polynucleotide sequence encoding one or more epitopes of hemaglutinin of ISAV. In preferred embodiments, the method further comprises maintaining suitable conditions for the yeast cells to express sub-viral particles comprising the VP2 capsid protein of IPNV and one or more epitopes of hemaglutinin of ISAV.

Another embodiment of the present invention provides a method of making sub-viral particles (SVP) comprising a VP2 capsid protein of IPNV and one or more epitopes of hemaglutinin of ISAV comprising transforming yeast cells with an expression vector comprising (i) a polynucleotide sequence encoding a VP2 capsid protein of IPNV and (ii) a polynucleotide sequence encoding one or more epitopes of hemaglutinin of ISAV; and purifying the sub-viral particles.

Another embodiment of the present invention provides a method of making sub-viral particles (SVP) comprising a VP2 capsid protein of IPNV and one or more epitopes of hemaglutinin of ISAV comprising transforming yeast cells with an expression vector comprising (i) a polynucleotide sequence encoding a VP2 capsid protein of IPNV and (ii) a polynucleotide sequence encoding one or more epitopes of hemaglutinin of ISAV; and encapsulating the yeast and the expressed sub-viral particles fully or partially by one or more excipients that are effective to enhance the stability of the yeast cells (e.g., by using MicroMatrix® technology).

The following examples are provided to describe the invention in greater detail and are intended to illustrate, not limit, the invention.

EXAMPLES

Example 1

Sequence Analysis of ISAV Hemaglutinin (HA) Gene

Sixty-nine nucleotide and amino acid sequences of the hemaglutinin (HA) gene of ISAV isolates were downloaded from GenBank database. Three redundant sequences were identified, leaving behind 66 unique sequences. Amino acid sequences of these entries were submitted to the program Antigenic to identify candidate antigenic regions (Table 1 below). Out of 66 unique sequences, only nine sequences had full-length HA gene sequences. These sequences were aligned using ClustalW2, and phylogenetic analysis was performed using the multiple the alignment file and an UPGMA program. Based on the phylogentic analysis, the protein sequences of two ISAV isolates that are not closely related were taken for hydrophilicity analysis, Hopp-Woods hydrophilicity plots were computed to identify regions likely exposed on the surface, and thus potentially antigenic, Finally, the nucleotide sequences representing three candidate epitopes (referred to herein as Epitope 1, Epitope 2, and Epitope 3) were taken for cloning in the IPNV VP2 backbone.

Example 2

Cloning of ISAV Epitopes in IPNV SVP Backbone and Western Blot Analysis

Figure 2A:
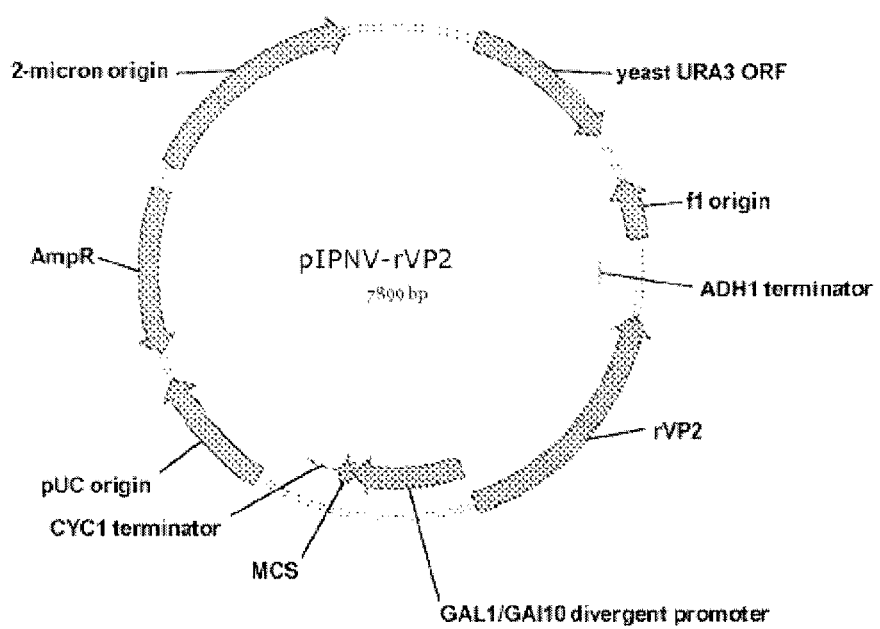
FIG. 2 illustrates vector maps of IPNV rVP2 sVLP (A) and IPNV/ISAV sVLP (B) constructs in a yeast expression vector. The IPNV VP2 gene was first cloned into pESC-URA vector (FIG. 2A) and ISAV epitopes were introduced at amino acid position 252 (FIG. 2B) and 286 (FIG. 2C) in the VP2 gene.

The cloning of IPNV VP2 gene in a yeast expression vector pESC-ura (Stratagene, San Diego, Calif.) was previously described (Allnutt et al., 2007). The resulting IPNV rVP2 clone was designated as pIPA1-Z1 (FIG. 2A). It has been reported that in the VP2 capsid protein of IPNV, the N-terminal amino acid positions between 241 and 288 are highly variable. In addition, the amino acid positions at 252 and 286 are on the surface of the capsid protein and these sites are flexible to accommodating a foreign epitope (Dhar et al., 2010). Subsequently, it was demonstrated that a heterologous epitope cloned at position 252 indeed elicited antibody response in rainbow trout (Dhar et al., 2010). Three ISAV epitopes (Epitopes 1, 2 and 3) were cloned each at amino acid positions 252 (nucleotide position 756) and 286 (nucleotide position 858) in the VP2 gene. Thus, six different recombinant clones were made.

The ISAV epitopes were cloned into 1426 nts IPNV VP2 gene (pIPA1-Z1 plasmid) by restriction digestion and overlapping PCR. First, pIPA1-Z1 plasmid DNA was digested with two unique restriction enzymes that are located at nucleotide positions 465 and 993. In order to clone the ISAV epitope at amino acid positions 252 (nucleotide position 756), a 292 base pair amplicon spanning the nucleotide positions 465 to 756 was amplified by PGR using the primers (Spe I VP2R/Ep1 VP2 252F, the italics sequence represent the ISAV epitopes 1, 2 and 3). Similarly, a 237 bp amplicon spanning the region between 756 and 993 was amplified by PCR using the primers Ep1 VP2 252R/PshA I VP2F. These two amplicons were then amplified by overlapping PCR using the primers Spe I VP2R and PshA I VP2F. The amplicon was digested with the restriction enzymes Spe I and PshA I and ligated to pIPA1-Z1 plasmid previously digested with the homologous enzymes, resulting in clones that contain ISAV epitopes at amino acid positions 252 (nucleotide position 756) in the IPNV VP2 gene (FIG. 2B).

In order to clone the ISAV epitope at amino acid positions 286 (nucleotide position 858), a 394 base pair amplicon spanning the nucleotide positions 465 to 858 was amplified by PCR using the primers (Spe I VP2R/Ep1 VP2 286F, the italics sequence represent the ISAV epitopes 1, 2 and 3). Similarly, a 136 bp amplicon spanning the region between 858 and 993 was amplified by PCR using the primers Ep1 VP2 286R/PshA I VP2F. These two amplicons were then amplified by overlapping PCR using the primers Spe I VP2R and PshA I VP2F, digested with the restriction enzymes Spe I and PshA I and ligated to pIPA1-Z1 plasmid previously digested with the homologous enzymes resulting clones that contain ISAV epitopes at amino acid positions 286 (nucleotide position 756) in the IPNV VP2 gene (FIG. 2C). Table 2 below provides nucleotide sequence of the primers used to clone ISAV epitopes into the IPNV VP2 gene by overlapping PCR.

The plasmid DNA was isolated from the recombinant chimeric IPNV/ISAV clones and sequenced. The recombinant plasmid was then used to transform yeast (*Saccharomyces cerevisiae* strain YPH501, Stratagene, La Jolla, Calif.) using a published protocol Agilent Technologies, Santa Clara, Calif.), After transformation, the transformants were plated on SG-dropout media and grown at 30° C. for two days before western blot analysis.

The western blotting of IPNV SVP and IPNV/ISAV chimeric SVP were performed following a published protocol (Allnutt et al., 2007). Briefly, recombinant yeast (*Saccharomyces cerivisiae* strain YH501; Stratagene, La Jolla, Calif.) clones were grown in autotrophic SG-ura medium containing galactose, yeast extract without amino acids, and amino acid dropout mixture (all amino acids plus adenine, no uracil) at 30° C. for 4 days. Cells were collected by centrifugation, and crude protein extracts were prepared using Y-PER yeast breaking buffer (Pierce Biotechnology, Rockford, Ill.). An aliquot of total protein was electrophoresed in a 12% SDS-polyacrylamide gel (BioRad, Richmond, Calif.) and transferred to PVDF membrane by electroblotting. The blots were probed with sheep-anti-IPNV polyclonal antibody (Microtek International, Inc, Saanichton, B.C., Canada) and detected with rabbit-anti-sheep polyclonal antibody conjugated to HRP (Bethyl Laboratories, Montgomery, Tex.). Detection was obtained using a ECL Plus Western Blotting Reagent Pack (GE Healthcare, Piscataway, N.J.).

Example 3

Purification of IPNV SVP and IPNV/ISAV Chimeric SVPs and Transmission Electron Microscopy IPNV as well as IPNV/ISAV SVPs were purified following essentially the same protocols as described for IPNV VP2 SVP (Allnutt et al., 2007). Briefly, recombinant yeast was grown inautotrophic SG-ura medium as described above at 30° C. for 4 days. Cells were then collected by centrifugation, treated with P-glucoronidase to prepare the protoplast following a published protocol (Pannunzio et al., 2004) before storing at −20° C. Protoplasted cells were then lysed by three freeze thaw (3 cycles), and then sonicated by 60 second pulses with 20 second intervals (5 cycles). The sample was then centrifuged at 10,000 rpm for 20 minutes at 4° C. The supernatant was layered over 15-60% (w/v) sucrose gradient and centrifuged at 28,000 rpm for 3 hours at 4° C. in a swinging bucket rotor (Beckman SW20). Multiple fractions were collected throughout the gradient. These include a layer at the very top of the gradient, fractions at 15%, 25%, 30%, 45% and 60% sucrose for ELISA assay using anti-IPNV antibody. All fractions were diluted 1:10 volume using TN buffer (50 mM Tris and 100 mM NaCl, pH 8.0) and tested by ELISA following a published protocol (Dhar et al, 2010). The fraction above 45% sucrose that formed a band and gave the highest reading in ELISA was centrifuged at 28,000 rpm for 2 hours at 4° C. in a swinging bucket rotor (Beckman SW20). The pellet was collected and suspended in TN buffer before using for transmission electron microscopy (TEM). TEM of the SVPs was performed according to previously published protocols (Dykstra, 1992).

Example 4

Preparation of Vaccine, Oral Immunization and Sampling of Rainbow Trout

In order to prepare the oral vaccine, recombinant yeast expressing either IPNV SVP or IPNV/ISAV SVP carrying different ISAV HA epitopes were grown as described above. Recombinant yeast cells were pelleted and the IPNV/ISAV SVP clones were mixed before encapsulation as described below. IPNV/ISAV SVP clones containing Epitope 1 at amino acid positions 252 and 286 were mixed in equal amount to form the treatment group 1. Similarly, IPNV/ISAV SVP clones containing Epitope 2 at amino acid positions 252 and 286 were mixed to form the treatment group 2, and IPNV/ISAV SVP clones containing Epitope 3 at amino acid positions 252 and 286 were mixed to form the treatment group 3. Finally, group 4 was represented by mixing the recombinant yeast expressing IPNV/ISAV SVP Epitopes 1, 2 and 3 in equal amount. Altogether there were eight treatment groups:
  Group 1: IPNV/ISAV SVP Epitope 1
  Group 2: IPNV/ISAV SVP Epitope 2
  Group 3: IPNV/ISAV SVP Epitope 3
  Group 4: IPNV/ISAV SVP Epitope 1+2+3
  Group 5: IPNV SVP
  Group 6: MicroMatrix® encapsulated non-recombinant yeast
  Group 7: Empty MicroMatrix®
  Group 8: non-vaccinated fish (healthy control).

The encapsulations of recombinant yeasts were carried out following MicroMatrix® Technology of Advanced BioNutrition Corp., Columbia, Md. and published protocols (Tobar et al., 2011; Harel, 2009). After encapsulation, the vaccine was top coated on rainbow trout diet using cod liver oil (Finfish Starter 55-15, #2 Crumble, Zeigler Bros, Gardners, Pa.).

Rainbow trout (av. weight 15 gm) was obtained from Albert Powell Hatchery, Hagerstown, Md. and acclimatized for two weeks before starting the experiments. During the entire course of the vaccine trial, water qualities were monitored three times a week and a daily water exchange of approx. 20% was carried out on a continuous basis. Fish were vaccinated by feeding MicroMatrix® encapsulated feed as well as control feed at a 3% of average body wt/day. The daily ration was divided between two feedings, one in the morning and one in the afternoon. Upon feeding, the fish were monitored to check that the feed was totally consumed. There were 15 fish per treatment of which 7 fish were sampled at day 41 and the remaining fish were sacrificed at termination of the experiment. Initial feeding of vaccine coated feed was done for 10 days (Day 1-Day 10). Thirty days following the initial feeding (i.e. on Day 41), fish (N=7 per treatment) were sampled by drawing blood to determine anti-IPNV and anti-ISAV antibody titer. Booster feeding was then carried out for ten days (Day 41-Day 50) before terminating the experiments at 30 days post-booster feeding (i.e. at Day 81). Blood samples were drawn at termination of the experiment to determine the anti-IPNV and anti-ISAV antibodies.

Example 5

Enzyme Linked Immunosorbent Assay (ELISA)

ELISA was performed to detect anti-IPNV and anti-ISAV antibody response in immunized rainbow trout essentially following a previously published protocol (Dhar et al., 2010). In order to detect anti-IPNV antibody, Immuno Breakapart microplates (Nunc, Rochester, N.Y.) were coated with lysate from recombinant protoplasted yeast expressing IPNV VP2 SVPs at 150 µg total protein/mL in a 50 mM carbonate coating buffer (pH 9.6) at 4° C. for 16 h. To detect anti-ISAV antibody response, Immuno Breakapart microplates were coated with 100 µl of peptide solution that contained a mixture of the three peptides (at 800 ng of each peptide/well) representing the ISAV epitopes 1, 2 and 3 (Epitope 1: N'-LLAPVYSRLLAPVYSR-C' (SEQ ID NO: 27); Epitope 2: N'-RGDVRVTPRGDVRVTP-C' (SEQ ID NO: 28); Epitope 3: N'-NKCVNKCVNKCVNKCV-C' (SEQ ID NO: 29)). ISAV peptides were custom synthesized (Genscript USA Inc., Piscataway, N.J.). After coating, the plates were washed 3 times in PBST (1× Phosphate Buffered Saline (PBS, 0.02M, pH 7.4)+0.05% Tween 20) for 5 min each wash. The plates were then blocked with 150 µl of 1×PBS containing 3% BSA for 3 hrs at room temperature. Test sera were diluted 1:32 and 1:64, 100 µl of the diluted sera were added per well before incubating the plates for 1 h at room temperature. Following incubation, the microplates were washed again 4 times with PBS (0.02M, pH 7.4) 0.05% Tween 20 for 5 min per wash. The primary antibody (mouse anti-salmonid IgG, Microtek International, Vancouver, British Columbia, Canada) was diluted to 1:1000 and 100 µl of the diluted antibody was added per well and incubated at room temperature for 1 hr. The plates were washed four times as described above. An HRP labeled goat anti-mouse IgG (EMD Biosciences, La Jolla, Calif.) was then diluted to 1:1000 and 100 µl was added per well. The plate was incubated at room temperature for 45 mins, washed four times and then detected by addition of the colorimetric substrate tetramethyl benzidine (TMB; 15 Pierce, Rockford, Ill.). The absorbance was read at 450 nm using a Spectrafluor Plus fluorescent plate reader (Tecan, Salzburg, Austria). Negative controls consisted of wells that were coated as above, but a 3% BSA solution was added instead of the fish serum during the capture step. Positive controls consisted of wells coated with purified IPNV rVP2 SVP and detected using IPNV polyclonal antibody (made against whole IPNV, Strain N1; Microtek International, B.C., Canada). A subset of samples (healthy control and empty micrometric control) was placed on each ELISA plate for normalization, giving us a scaling factor to allow plate-to-plate comparisons. Vaccinated fish were considered seropositive if their A450 values were above the mean adjuvant control +2 standard deviations. Comparisons among A450 values of different treatments were performed using a factorial ANOVA test followed by Fisher's PLSD test.

Example 6

Identification of ISAV Hemagglutinin Esterase (HE) Epitopes

ISAV genomic segment 6 is 1.3 to 1.5 kb in size and encodes a 38-43 kDa hemagglutinin esterase (HE) protein which has both the receptor-binding and receptor destroying enzyme activities (Krossoy et al. 2001, Rimstad et al, 2001; Falk at al, 2004). In HE gene, there is a highly polymorphic region (HPR) in the stalk of the protein near the transmembrane domain that varies among the geographic isolates of ISAV, and modulates the virulence of the virus (Cunningham et al., 2002; Mjaaland et al., 2002; Kibenge et al, 2007). Therefore, HE is a candidate gene to develop subunit and/or DNA vaccines. As described above, the nucleotide sequences of HE gene representing different geographic isolates of ISAV were obtained from the GenBank and submitted to the program Antigenic. Six candidate antigenic regions were identified (Table 1 below). An UPGMA analysis using nine full-length HE gene sequence clustered ISAV isolates into two major clusters, a European cluster (isolates from United Kingdom and Norway) and a North American cluster (an isolate from Canada, FIG. 1). The European cluster was further divided into two clusters. Subsequently, Hopp-Woods hydrophilicity plots were computed for two of the protein sequences (an isolate from Norway and a Canadian isolate) to identify regions likely exposed on the surface, and thus potentially antigenic. At the end, the nucleotide sequences representing three candidate epitopes were taken for cloning in the IPNV VP2 backbone.

Example 7

Cloning, Expression and Transmission Electron Microscopy (TEM) of IPNV/ISAV Chimeric VLP Expressed in Yeast Cloning of ISAV Epitopes in IPNV VP2 Backbone.

IPNV VP2 gene representing the predicted mature VP2 protein was cloned behind GAL10 promoter in pESC-ura (FIG. 2A). Subsequently, ISAV HE epitopes 1, 2 and 3 were cloned at amino acid positions 252 and 286 into VP2 gene, resulting in pIPNV/ISAV rVP2-252E1/E2/E3 (FIG. 2B) and pIPNV/ISAV rVP2-286E1/E2/E3 (FIG. 2C). Recombinant yeast clones containing IPNV VP2 gene as well as IPNV/ISAV chimeric VP2 genes were grown under galactose induction, then analyzed by western analysis to determine if VP2 is expressed. Total proteins from recombinant yeast clones were electrophoresed on 12% SDS-polyacrylamide gels, and western blot analysis performed using anti-IPNV antibody. A 55 kDa band representing IPNV/ISAV chimeric VP2 protein was detected in both pIPNV/ISAV rVP2-252 (FIG. 2B) and pIPNV/ISAV rVP2-286 clones (FIG. 2C).

Preparation of VLPs and Transmission Electron Microscopy (TEM).

Three representative clones, a pIPNV rVP2 clone, a pIPNV/ISAV rVP2-252E1 and a pIPNV/ISAV rVP2-286E3 were taken to purify SVP and determining the morphology and size by transmission electron microscopy (TEM). Using the methods described above. Several areas of high density were observed in the sucrose gradients. A high density band above 45% sucrose gave a strong positive reaction in ELISA using anti-IPNV antibody. This fraction was further pelleted by high speed centrifugation and examined by TEM. Particles with icosahedral morphology were observed for all three samples. This indicated that IPNV rVP2 assembled to form SVP, but also that IPNV/ISAV chimeric rVP2 were capable of self-assembling into SVP. Therefore, the addition of HE epitopes into IPNV VP2 backbone did not affect the tertiary structure of rVP2.

Example 8

Immunization of Rainbow Trout Using IPNV/ISAV SVP and Determining the Anti-IPNV and Anti-ISAV Antibody Responses Oral vaccination would provide a number of advantages over injection such as ease of use, ability to vaccinate smaller fish, lower cost of vaccine, and easy ability to make multivalent vaccines. In order to test the ability of IPNV rVP2 and chimeric IPNV/ISAV rVP2 to induce an immune response, recombinant yeast expressing SVPs were encapsulated using Advanced BioNutrition Corporation's MicroMatrix® technology and top coated onto rainbow trout feed. Initial feeding of the vaccinated feed was performed for 10 days and at day 41 post-vaccination fish were sampled. After sampling of fish, booster feeding was carried out for 10 days before terminating the experiment at day 81.

The anti-IPNV titers were determined in samples collected at days 41 and 81 and compared to that found in naive fish, fish fed a control feed coated with empty MicroMatrix® and fish fed a control feed supplemented with wild-type yeast in place of the recombinant yeast (FIG. 3). It was apparent that the orally vaccinated fish had an immune response greater than that observed in either naive or MicroMatrix® coated or yeast control fed fish. Anti IPNV antibody measured in oral vaccinated fish was significantly higher than fish in control groups at both 30- and 60-days post-vaccination (FIGS. 3A and 3B). It was interesting to note that the addition of ISAV antigenic epitope in IPNV SVP resulted in higher anti-IPNV antibody titer compared to fish vaccinated with IPNV SVP only. This showed that ISAV epitope had an effect similar to adjuvant in enhancing anti-IPNV antibody titer.

Figure 3A:
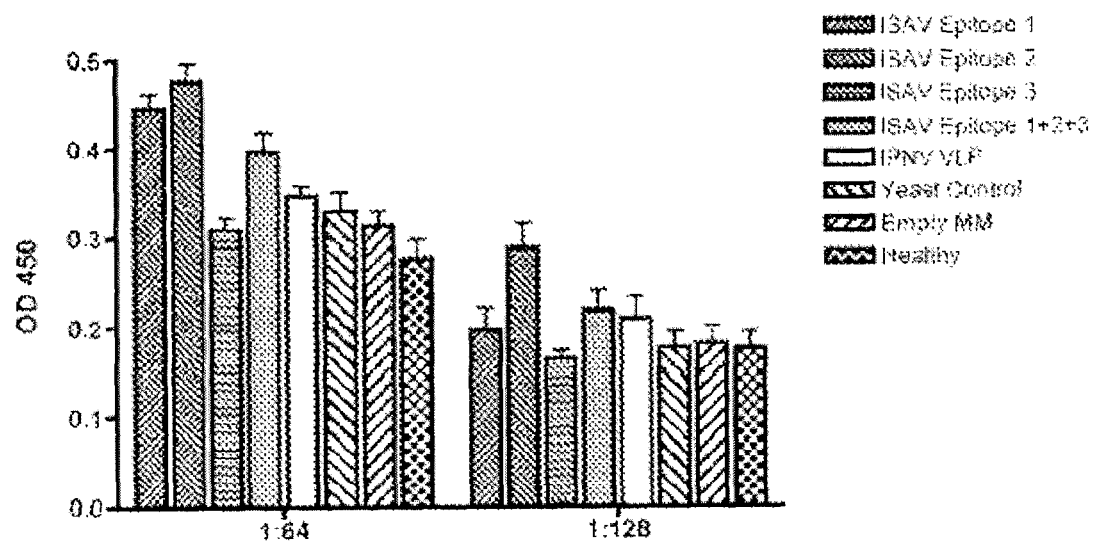
FIG. 3 illustrates an immunoassay of sera to determine the anti-IPNV (FIGS. 3A and 3B) and anti-ISAV (FIGS. 3C and 3D) responses in immunized rainbow trout using enzyme-linked immunosorbant assay (ELISA). The ELISA plate was coated with purified IPNV rVP2 SVP and mean ELISA values (A450) of anti-IPNV titer were detected in rainbow trout serum at day 30 (FIG. 3A) and at day 60 (FIG. 3B) post-vaccination via oral route. The ELISA plate was coated with ISAV peptide and mean ELISA values (A450) of anti-ISAV titer was detected in rainbow trout serum at day 30 (FIG. 3C) and at day 60 (FIG. 3D) post-vaccination via oral route.
Figure 3B:
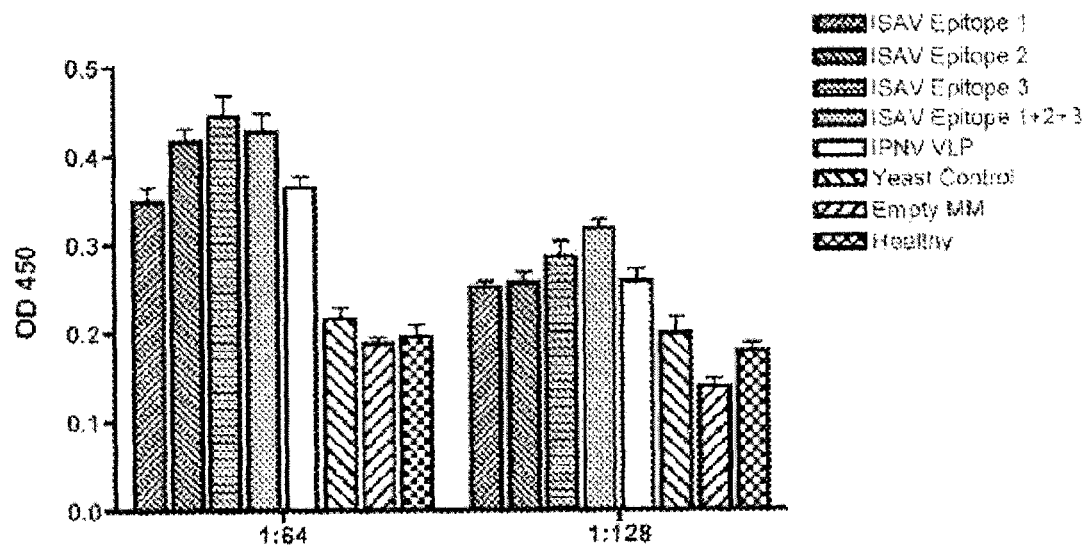
Figure 3C:
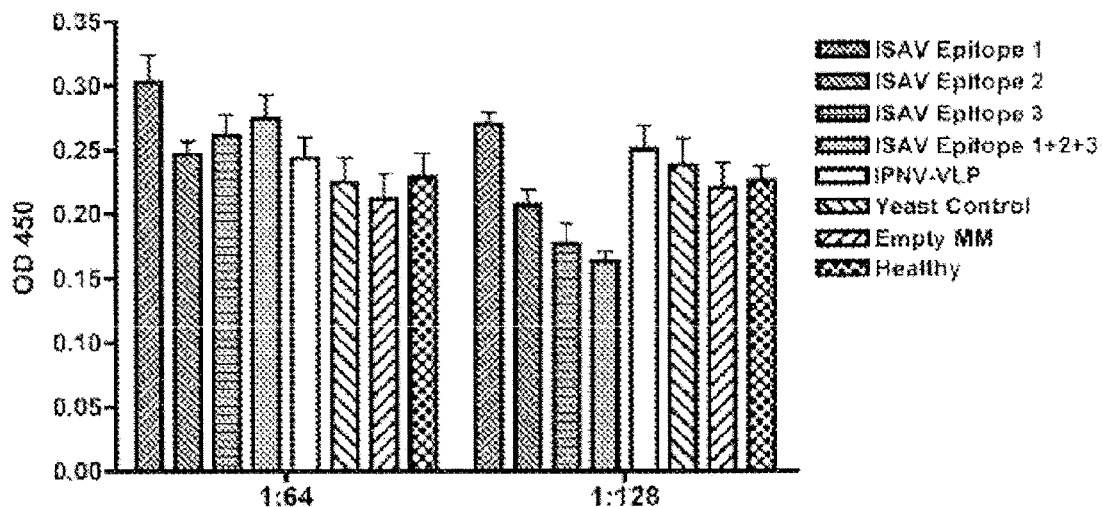
Figure 3D:
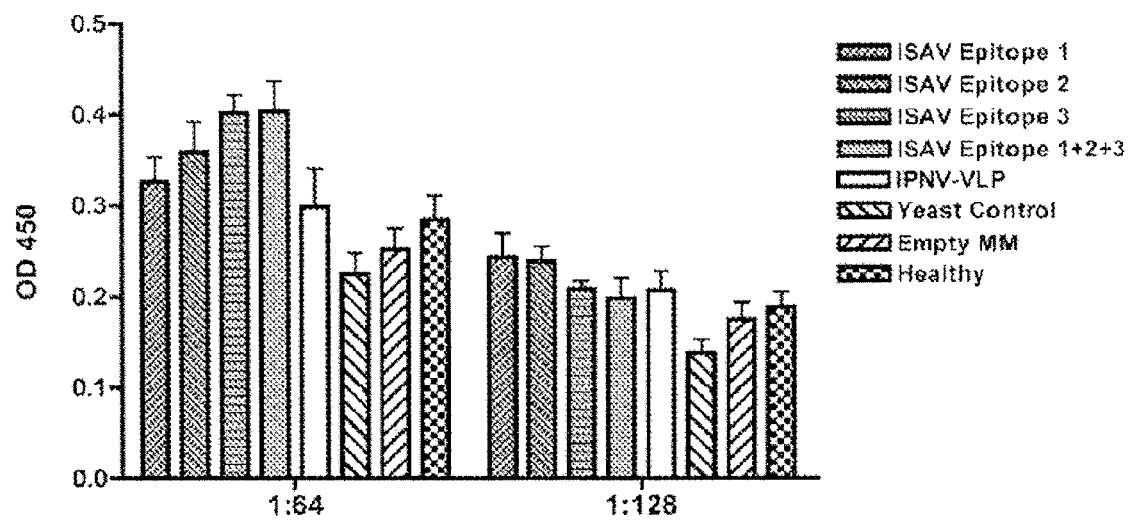

The anti-ISAV antibody was also detected in oral vaccinated fish at 41- and 81-days post-vaccination (FIGS. 3C and 3D). Overall, the level of anti-ISAV titer in oral vaccinated fish was higher at day 81 compared to day 41 post-vaccination. The detection of anti-ISAV antibody in oral vaccinated fish indicates that the ISAV epitopes were surface exposed on the IPNV SVP and recognized by the host immune system to elicit antibody response.

The data suggests that IPNV SVP can tolerate the incorporation of heterologous epitope without affecting the tertiary structure of the recombinant protein and antibody response against the backbone peptide and the foreign epitopes. This opens up the opportunity to using IPNV SVP as a platform to developing bivalent and potentially multivalent vaccine against viral diseases in salmonids such as IPN and ISA among others. These data indicate that oral vaccination could potentially provide an alternative to intraperitoneal or intramuscular injection vaccination for the treatment of IPN and ISA diseases.

Example 9

IPNV and ISAV Challenge Following Vaccination by Oral and Injection Routes

The efficacy of IPNV/ISAV SVP vaccine is determined by vaccinating fish either orally or by intraperitonial or intramuscular injection and then challenging the animals with live IPNV and ISAV. In order to use IPNV-ISAV SVP as an injectable vaccine, SVPs are purified from recombinant yeast, as described in the Example "Purification of IPNV SVP and IPNV/ISAV chimeric SVPs and transmission electron microscopy."

Vaccination by Injection and Oral Routes:

Rainbow trout (*Oncorhynchus mykiss*) and/or Atlantic salmon (*Salmo salar*) known to be free of IPNV and ISAV, are immunized by injecting purified IPNV/ISAV SVPs intraperitoneally (IP) with 100 μL of vaccine (50 μL of purified SVPs containing 100 μg of antigen and 50 μL of Freund's Complete Adjuvant; Sigma Fluka Aldrich, St. Louis, Mo.) following a published protocol (Dhar et al., 2010). Additionally, rainbow trout and/or Atlantic salmon are immunized by oral route following a published protocol (Tobar et al., 2010). Following primary and booster immunization protocol by injection and oral routes, as described in the Example "Preparation of vaccine, oral immunization and sampling of rainbow trout," blood samples are collected from vaccinated fish to determining the antibody response, as described in the Example "Immunization of rainbow trout using IPNV/ISAV SVP and determining the anti-IPNV and anti-ISAVantibody responses."

IPNV Challenge:

Following immunization, IPNV challenge are performed by injecting each fish with approximately 250 μL of $10^7$ $TCID_{50}$/mL of IPNV following a published protocol (Dhar et al, 2010). Naive fish injected with buffer served as the negative control for the IPNV challenge. Ten days post-injection, animals are sacrificed, spleen samples collected in TRI reagent (Molecular Research Center, Cincinnati, Ohio), and then stored at −75° C. until RNA isolation is performed to determining the IPNV load in the vaccinated fish and fish in control treatment(s).

ISAV Challenge:

ISAV challenge is performed following a cohabitation challenge model (Lauscher et al., 2011). Briefly, following booster vaccination and collection of blood samples to determine the anti-ISAV antibody, sentinel fish are injected with ISAV inoculum at $2.5\times10^3$ $TCID_{50}$/fish and cohabitated with control or vaccinated fish, following an ISAV cohabitation challenge model as described by Raynard et al. (2001). Fish mortality is evaluated daily and dead fish are evaluated for ISAV presence by histopathology following a published protocol (Lauscher et al., 2011). In addition, ISAV load in the head kidney tissue of vaccinated fish and fish in control treatment(s) are measured by real-time RT-PCR to further determining the efficacy of vaccination. Fish vaccinated with yeast expressing such chimeric SVP elicited immune response in the vaccinated fish and protected fish against ISAV and IPNV challenge.

Example 10

Determining IPNV and ISAV Load by Real-Time RT-PCR

In order to determining the efficacy of the vaccination, real-time RT-PCR is performed to determining the IPNV and ISAV load in the vaccinated fish and fish in control treatments.

IPNV Real-Time RT-PCR:

Total RNA is isolated from spleen tissue of control and IPNV-injected rainbow trout using TR1 reagent following the manufacturer's protocols (Molecular Research Center). The RNA samples are treated with DNase I (Ambion, Inc., Austin, Tex.) then the RNA quality assessed by running the samples on a 1% formaldehyde agarose gel (Sambrook et al., 1989). The cDNA synthesis and real-time RT-PCR is performed following a published protocol (Bowers et al., 2008). Briefly, cDNA is synthesized in a 40 μL reaction volume containing 1 μg total RNA, 1×RT-PCR buffer, 1 mM dNTPs, 0.75 μM oligo dT, 4 U of RNase inhibitor, and 5 U of MultiScribe reverse transcriptase (Applied Biosystems, Foster City, Calif.) at 42° C. for 1 h. The cDNA is diluted 1:10 using DNase and RNase free molecular biology grade water and 2 μL of the diluted cDNA used per reaction in real-time RT-PCR.

IPNV real-time RT-PCR is performed using a Bio-Rad iCycler iQ™ (Bio-Rad Laboratories, Inc., Richmond, Calif.), and following a previously published protocol (Bowers et al., 2008). The primers for real-time RT-PCR are designed based on the nucleotide sequence of Segment A of IPNV genome (GenBank accession number NC_001915), and the internal control genes, β-actin (AF157514) and elongation factor 1-α (EF-1α, AF498320). The primer sequences for IPNV are 1916F: 5'-AGGAGATGAC ATGTGCTACA CCG-3' (SEQ ID NO: 30) and 1999R: 5' CCAGCGAATA TTTTCTCCAC CA-3' (SEQ ID NO: 31), for rainbow trout β-actin are 1301F: 5'-TGCTTCACCG TTCCAGTTGT G-3' (SEQ ID NO: 32), and 1413R: 5'-TGCTTCACCG TTCCAGTTGT G-3' (SEQ ID NO: 33) and for EF-1a are 136F: 5'-TGATCTACAA GTGCGGAGGC A-3' (SEQ ID NO: 34) and 236R: 5'-CAG-CACCCAG GCATACTTGA A-3' (SEQ ID NO: 35).

The primer sequences of the control gene in Atlantic salmon can be obtained from a previously published paper (Jorgensen et al., 2006). The reaction mixture for real-time RT-PCR contains 12.5 μL of 2×SYBR Green Supermix (iQ 5 SYBR Green Supermix), 300 nM each of forward and reverse primers, and 2 μL of the 1:10 diluted cDNA in a 25 μL reaction volume. The amplifications are carried out in a 96 well plate and each sample has 3 replicates. The thermal profile for real-time RT-PCR is 95° C. for 10 minutes, followed by 40 cycles of 95° C. for 10 seconds and 60° C. for 1 minute.

After each run, data acquisition and subsequent data analyses are performed using the iCycler iQ Real-Time PCR Detection System (Biorad iQ Software Version 1.3). The relative IPNV load in a sample is measured by subtracting the mean $C_t$ values for β-actin and EF-1α from the mean Q values of the IPNV amplicon. The differences in the Q value of the viral genes and the corresponding internal controls is expressed as $\Delta C_t$. The difference in the $\Delta C_t$ for one vaccine group compared to the $\Delta C_t$ of the corresponding control is expressed as $\Delta\Delta C_t$, and $2^{\Delta\Delta Ct}$ represented the difference in the viral load between the two treatments.

ISAV Real-Time RT-PCR:

The protocol for determining the ISAV load by real-time RT-PCR in the vaccinated and control fish is very similar to the protocol of determining the IPNV load as described above, except that the primers for ISAV detection and quantification is based on the ISAV gene such as matrix protein or hemagglutinin. Real-time RT-PCR has shown to be a very sensitive and reproducible tool to detecting and quantifying ISAV infection (Workenhe et al. 2008) in salmonid fish. The data analysis to determine the relative load of ISAV is also similar to IPNV data analysis, as described above.

TABLE 1

Nucleotide sequence (SEQ ID NOS. 1-6) and peptide sequence (SEQ ID NOS. 7-12) of candidate antigenic regions of ISAV hemagglutinin esterase (HE) gene.

| Potential epitopes | Nucleotide Sequence (5'-3') | 5'-end | 3'-end | Average anti-genicity score | Hydrophilic peak (at nucleotide |
| --- | --- | --- | --- | --- | --- |
| Epitope 1 | CTGTTGGCGCCTGTTTACAGTCGC (SEQ ID NO: 1)<br>LLAPVYSR (SEQ ID NO: 7) | 28 | 52 | 1.203 | — |
| Epitope 2 | AGGGGAGACGTGAGAGTGACGCCT (SEQ ID NO: 2)<br>RGDVRVTP (SEQ ID NO: 8) | 355 | 379 | 1.167 | 363 |
| Epitope 3 | AACAAGTGTGTT (SEQ ID NO: 3)<br>NKCV (SEQ ID NO: 9) | 655 | 668 | 1.171 | 657 |
| Epitope 4 | TTTTCGGTGAAGGTGTTGACTTTC (SEQ ID NO: 4)<br>FSVKVLTF (SEQ ID NO: 10) | 436 | 460 | 1.191 | — |
| Epitope 5 | ATCTACAAGGTCTGCATTGCA (SEQ ID NO: 5)<br>IYKVCIA (SEQ ID. NO: 11) | 505 | 526 | 1.179 | — |
| Epitope 6 | TTTGGGATTGCTCTGTTCCTA (SEQ ID NO: 6)<br>FGIALFL (SEQ ID NO: 12) | 1076 | 1100 | 1.118 | — |

TABLE 2

Nucleotide sequence of the primers used to clone ISAV epitopes in IPNV VP2 gene by overlapping PCR.

| Primer name | Nucleotide sequence (5'-3') | SEQ ID NO. |
| --- | --- | --- |
| PshA I VP2F | CCTGATGAGAATGAGACTGAC GCGGGTCCTTTGGC | 13 |
| Spe I VP2R | CCCTCAGGACAAGGTCAACAA CCAACTAGTGACCAAAGG | 14 |
| Ep1 VP2 252R | CTGTTGGCGCCTGTTTACAGT CGCAACGAGACGCGGTTCG | 15 |
| Ep1 VP2 252F | GCGACTGTAAACAGGCGCCAA CAGGACGGGTTCGGCTGC | 16 |
| Ep2 VP2 252R | AGGGGAGACGTGAGAGTGACG CCTAACGAGACGCGGTTC | 17 |
| Ep2 VP2 252F | AGGCGTCACTCTCACGTCTCC CCTGACGGGTTCGGCTGC | 18 |
| Ep3 VP2 252R | AACAAGTGTGTTGACGGGTTC GGCTGCTAGTTGGAAG | 19 |
| Ep3 VP2 252F | AACACACTTGTTGACGGGTTC GGCTGCTAGTTGGAAG | 20 |
| Ep1 VP2 286R | CTGTTGGCGCCTGTTTACAGT CGCTACAGGGGTGCCTCC | 21 |
| Ep1 VP2 286F | GCGACTGTAAACAGGCGCCAA CAGGTTGTCGGCCGTGAC | 22 |
| Ep2 VP2 286R | AGGGGAGACGTGAGAGTGACG CCTACAGGGGTGCCTCC | 23 |
| Ep2 VP2 286F | AGGCGTCACTCTCACGTCTCC CCTGTTGTCGGCCGTGAC | 24 |
| Ep3 VP2 286R | AACAAGTGTGTTGTTGTCGGC CGTGACCAGGGTTGAGC | 25 |
| Ep3 VP2 286F | AACAAGTGTGTTTACAGGGGT GCCTCCGCCAAGTTTAC | 26 |

SEQUENCE LISTING FREE TEXT

The artificial sequences provided herein (i.e., SEQ ID NOS. 13-30), such as nucleotide sequences for primers, are completely synthesized. The term "Completely Synthesized" is used in the Sequence Listing submitted herewith to describe artificial sequences.

REFERENCES

The contents of all references cited herein are incorporated by reference herein in their entireties and for all purposes.

1. Allnutt, F. C., Rowe, C., Bowers, R. M., Vakharia, V., LaPatra, S. E. and Dhar, A. K. 2007. Antigenicity of infectious pancreatic necrosis virus VP2 sub-viral particle expressed in yeast. Vaccine 25: 4880-4888.
2. Bowers, R. M., LaPatra, S. E., Dhar, A. K., 2008. Detection and quantification of infectious pancreatic necrosis virus by real-time reverse transcriptase polymerase chain reaction using lethal and non-lethal sampling. J. Virol. Methods 147, 226-234.
3. Chackerian, B. 2007. Virus-like particles: flexible platforms for vaccine development. Expert. Rev. Vaccines 6: 381-390.
4. Cotte, L., Rivas, A., Cortez, M., Sandino, A. M., and Spencer, E. 2010. Infectious salmon anemia virus-Genetics and pathogenesis. 2010. Virus Res. 155: 10-19.

5. Cunningham, C. O., Gregory, A., Black, J., Simpson, I., and Raynard, R. S. 2002. A novel variant of the infectious salmon anemia virus (ISAV) haemagglutinin gene suggests mechanisms for virus diversity. Bull. Eur. Assoc. Fish Pathol. 22: 366-374.
6. Dhar, A. K., Bowers, R. A., Rowe, C., and Allnutt, F. C. T. 2010. Expression of a foreign epitope on infectious pancreatic necrosis virus VP2 capsid protein sub-viral particle (SVP) and immunogenicity in rainbow trout. Antiviral Res. 85: 525-531.

7. Dobos, P., Hallett, R., Kells, D. T., Sorensen, O., and Rowe, D. 1997. Biophysical studies of infectious pancreatic necrosis virus. J. Virol. 22: 150-159.

8. Duncan, R., Nagy, E., Krell, P. J., and Dobos, P. 1987. Synthesis of the infectious pancreatic necrosis virus polyprotein, detection of a virus-encoded protease, and fine structure mapping of genome segment A coding regions. J. Virol. 61: 3655-64.

9. Falk, K., Aspehaug, V., Vlasak, R., and Endresen, C. 2004. Identification and characterization of viral structural proteins of infectious salmon anemia virus. J. Virol. 78: 30633071.

10. Frost P., Havarstein, L. S., Lygren, B., Stahl, S., Endresen, C. and Christie, K. E. 1995. Mapping of neutralization epitopes on infectious pancreatic necrosis viruses. J. Gen. Virol. 76: 1165-1172.

11. Garcea, R. L. and Gissmann, L. 2004. Virus-like particles as vaccines and vessels for the delivery of small molecules. Curr. Opin. Biotech. 15: 513-517.

12. Grgacic, E. V. L. and Anderson, D. A. 2006. Virus-like particles: Passport to immune recognition. Methods 40: 60-65.

13. Gilbert, L., Toivola, J., White, D., Ihalainen, T., Smith, W., Lindholm, L., Vuento, M., and Oker-Blom, C. 2005. Molecular and structural characterization of fluorescent human parvovirus B19 virus-like particles. Biochem Biophys Res Commun. 331: 527-535.

14. Gomez-Casado, E., Estepa, A. and Coll, J. M. 2011. A comparative review on European-farmed finfish RNA viruses and their vaccines. Vaccine 29: 2657-2671.

15. Harel, M. 2009. Encapsulated vaccines for the oral vaccination and boostering of fish and other animals. US Patent Application Number US20090238845.

16. Harper, D. M., Franco, E. L., Wheeler, C. M. et al. 2006. Sustained efficacy up to 4.5 years of a bivalent LI virus-like particle vaccine against human papilloma virus types 16 and 18: follow-up from a randomized control trial. Lancet 367: 1247-1255.

17. Heppell J., E. Tarrab, J. Lecomte, L. Berthiaume, and M. Arella. 1995. Strain variability and localization of important epitopes on the major structural protein (VP2) of infectious pancreatic necrosis virus. Virology 214: 40-49.

18. Hernando, E., Llamas-Saiz, A. L., Foces-Foces, C., McKenna, R., Portman, I., Agbandje-McKenna, M., and Almendral, J. M. 2000. Biochemical and physical characterization of parvovirus of minute virus of mice virus-like particles. Virology 267: 299-309.

19. Hou, L., Wu, H., Xu, L. and Yang, F. 2009. Expression and self-assembly of virus-like particles of infectious hypodermal hematopoietic necrosis virus in *Escherichia coli*. Arch. Virol.

20. Houston, R. D., Gheyas, A., Hamilton, A., Guy, D. R., Tinch, A. E., Taggart, J. B., McAndrew, B. J., Haley, C. S., and Bishop, S.C. 2008. Detection and confirmation of a major QTL affecting resistance to infectious pancreatic necrosis (IPN) in Atlantic salmon (*Salmo salar*) Anim. Genomics Anim. Health 132: 199-204.

21. Jorgensen, S. M., Clevalend, E. J., Grimholt, U., and Gjoen, T. 2006. Validation of reference genes for real-time polymerase chain reaction studies in Atlantic salmon. Mar. Biotechnol. 8: 398-408.

22. Kawaoka, Y., Cox, N. J., Kaverin, N., Klenk, H. D., Lamb, R. A., Mccauley, J., Nakamura, K., Palese, P., and Webster, R. G. 2005. Family Orthomyxoviridae. In: Faquet, C., Mayo, M. A., Maniloff, J., Desselberger, U., and Ball, L. A. (Eds.), Virus Taxomony: Classification and nomenclature of viruses. VIIIth Report of the International Committee on Taxonomy of Viruses. Elsevier Academic Press, San Diego, Calif., pp. 681-693.

23. Kibenge, F. S., Munir, K., Kibenge, M. J., Joseph, T., and Moneke, E. 2004. Infectious salmon anemia virus: Casautive agent, pathogenesis and immunity. Anim. Health Res. Rev. 5: 6578.

24. Kibenge, F. S., Kibenge, M. J., Wang, Y., Qian, B., Hariharan, S., and McGeachy, S. 2007. Mapping of putative virulence motifs on infectious salmon anemia virus surface glycoprotein gens. J. Gen. Virol. 88: 3100-3111.

25. Krossoy, B., Devoid, M., Sanders, L., Knappskog, P. M., Aspehaug, V., Falk, K., Nylund, A., Koumans, S., Endresen, C, and Biering, E. 2001. Cloning and characterization of the infectious salmon anemia virus haemagglutinin. J. Gen. Virol. 82: 1757-1765.

26. Labus, M. B., Breeman, S., Ellis, A. E., Smail, D. A., Kervick, M., and Melvin, W. T. 2001. Antigenic comparison of a truncated form of VP2 of infectious pancreatic necrosis (IPN) virus expressed in four different cell types. Fish & Shellfish Immunol. 11: 203-216.

27. Landry, N., Ward, B. J., Trepanier, S., Montomoli, E., Dargis, M., Lapini, G., and Vezina, L. P. 2010. Preclinical and clinical development of plant-made virus-like particle vaccine against avian H5N1 influenza. PLoS One 5(12): e15559.

28. Lauscher, A., Krossoy, B., Frost, P., Grove, S., Konig, M., Bohlin, J., Falk, K., Austbol, L., and Rimstad, E. 2011. Immune response in Atlantic salmon (*Salmo salar*) following protective vaccination against infectious salmon anemia (ISAV) and subsequent ISA virus infection. Vaccine, In press.

29. Magyar, G., and P. Dobos. 1994. Evidence to the detection of the infectious pancreatic necrosis virus polyprotein and the 17 kDa polypeptide in infected cells and the NS protease in purified virus. Virology 204: 580-589.

30. Mao, C., Koutsky, L. A., Ault, K. A. 2006. Efficacy of human papilloma virus-16 vaccine to prevent cervical intraepithelian neoplasia: a randomized control trial. Obstet. Gynecol. 107: 18-27.

31. Mjaaland, S., Hungnes, O., Teig, A., Dannevig, B. H., Thorud, K. and Rimstad, E. 2002. Polymorphism in the infectious salmon anemia virus haemagglutinin gene: importance and possible implications for evolution and ecology of infectious salmon anemia disease. Virology 304: 379-391.

32. Muller, A., Markussen, T., Drablos, F., Gjoen, T., Jorgensen, T. O., Solem, S. T., and Mjaaland, S. 2010. Structural and functional analysis of the hemagglutinin-esterase of infectious salmon anemia virus. Virus Res. 151: 131-141.

33. Ozaki, A., Sakamoto, T., Khoo, S., Nakamura, K., Coimbra, M. R., Akutsu, T., and Okamoto, N. 2001. Quantitative trait loci (QTLs) associated with resistance/susceptibility to infectious pancreatic necrosis virus (IPNV) in rainbow trout (*Oncorhynchus mykiss*). Mol. Gen. Genet. 265:23-31.

34. Pannunzio, V. G., Burgos, H. I., Alonso, M., Ramos, E. H., Mattoon, J. R., Stella, C. A. 2004. Yeast Plasmids with the Least Trouble. Promega Notes 87: 27-28.
35. Pederson, T., Skjesol, A., and Jorgensen, J. B. 2007. VP3, a structural protein of infectious pancreatic necrosis virus, interacts with RNA-dependent RNA polymerase VP1 and with double-stranded RNA. J. Virol. 81: 6652-6663.
36. Pous, J., C. Chevalier, M. Ouldali, J. Navaza, B. Delmas and J. Lepault. 2005. Structure of bimavirus-like particles determined by combined electron cryomicroscopy and X-ray crystallography. J. Gen. Virol. 86: 2339-2346.
37. Ramanos, M. A., C. A. Scoer, and J. J. Clare. 1992. Foreign gene expression in yeast: a review. Yeast 8: 423-488.
38. Raynard, R. S., Snow, M., and Bruno, D. W. 2001. Experimental infection model and susceptibility of Atlantic salmon (*Salmo salar*) to a Scotish isolate of infectious salmon anemia virus (ISAV). Dis Aquat Org. 47: 169-174.
39. Remond, M., Costa B. D., Riffault, S., Parida, S., Breard, E., Lebreton, F., Zientara, S, and Delmas, B. 2009. Infectious bursal disease subviral particles displaying the foot-and-mouth disease virus major antigenic site. Vaccine 27: 93-98.
40. Rimstad, E., Mjaaland, S., Snow, M., Mikalsen, A. B., and Cunningham, C. O. 2001. Characterization of the infectious salmon anemia virus genome segment that encodes the putative haemagglutinin. J. Virol. 75: 5352-5356.
41. Sambrook, J., Fritsch, E. F., Maniatis, T., 1989. Molecular Cloning: A Laboratory Manual. Second ed. Cold Spring Harbor, N.Y.: Cold Spring Harbor Laboratory.
42. Santi, N., Vakharia, V. N., Evensen, O. 2004. Identification of putative motifs involved in the virulence of infectious pancreatic necrosis virus. Virology 322: 31-40.
43. Sedlik, C, Saron, M., Sarrascea, J., Casal, I., and Leclerc, C. 1997. Recombinant parvovirus-like particles as an antigen carrier: a novel non-replicative exogenous antigen to elicit protective antiviral cytotoxic T cells. Proc. Natl. Acad. Sci. USA 94: 7503-7508.
44. Shivappa, R. B., P. E. McAllister, G. H. Edwards, N. Santi, O. Evensen, and V. N. Vakharia. 2005. Development of a subunit vaccine for infectious pancreatic necrosis virus using a baculovirus insect/larvae system. In: P. J. Midtlyng (ed.) Progress in Fish Vaccinology. Dev. Biol. Basel 121: 165-174.
45. Sundh, H., Olsen, R-E., Fridell, F., Gadan, K., Evensen, O., Glette, J., Taranger, G-L., Myklebust, R., and Sundell, K. 2009. The effect of hyperoxygenation and reduced flow in fresh water and subsequent infectious pancreatic necrosis virus challenge in sea water, on the barrier integrity in Atlantic salmon (*Salmo salar*). J. Fish Dis. 32: 687-698.
46. Thorud, K. E., and Djupvik, H. O. 1988. Infectious salmon anaemia in Atlantic salmon (*Salmo salar*). Bull. Eur. Assoc. Fish Pathol. 8: 109-111.
47. Tobar, J. A., Contreras, F. C, Betz, Y. M., Bravo, C, Caruffo, M., Jerez, S., Goodrich, T., and Dhar, A. K. 2010. Oral vaccination against infectious salmon anemia in atlantic salmon (*salmo salar*) induces specific immunity and provides protection against infectious salmon anemia virus challenge. World Aquaculture Society Meeting, San Diego, Calif.
48. Tobar, J. A., Jerez, S., Caruffo, S., Bravo, C, Contreras, F., Bucarey, S. A., and Harel, M. 2011. Oral vaccination of Atlantic salmon (*Salmo salar*) against salmonid rickettsial septicaemia. Vaccine 29: 2336-2340.
49. Workenhe. S. T., Kibenge. M. J., Iwamoto. T., and Kibenge. F. S. 2008. Absolute quantitation of infectious salmon anaemia virus using different real-time reverse transcription PCR chemistries. J Virol Methods. 154:128-34.

Although the present invention has been described in connection with specific embodiments, it should be understood that the invention as claimed should not be unduly limited to such specific embodiments. Indeed, various modifications and variations of the described compositions and methods of the invention will be apparent to those of ordinary skill in the art and are intended to be within the scope of the appended claims.

What is claimed is:

1. Yeast cells comprising an expression vector (i) a polynucleotide sequence encoding a VP2 capsid protein of infection pancreatic necrosis virus (IPNV) and (ii) a polynucleotide sequence encoding one or more epitopes of hemaglutinin of infectious salmon anemia virus (ISAV), wherein the one or more epitopes of hemagglutinin of ISAV is located at amino acid position 252 or 286 of the VP2 capsid protein.

2. Yeast cells comprising an expression vector comprising (i) a polynucleotide sequence encoding a VP2 capsid protein of infectious pancreatic necrosis virus (IPNV) and (ii) a polynucleotide sequence encoding one or more epitopes of hemaglutinin of infectious salmon anemia virus (ISAV), wherein the one or more epitopes of hemaglutinin comprise one or more amino acid sequences selected from the group consisting of: LLAPVYSR (SEQ ID NO: 7), RGDVRVTP (SEQ ID NO: 8), NKCV (SEQ ID NO: 9), FSVKVLTF (SEQ ID NO: 10), IYKVCIA (SEQ ID, NO: 11), FGIALFL (SEQ ID NO: 12), and a combination thereof.

3. The yeast cells of claim 2, wherein the one or more epitopes of hemagglutinin comprise one or more amino acid sequences selected from the group consisting of: LLAPVYSR (SEQ ID NO: 7), RGDVRVTP (SEQ ID NO: 8), NKCV (SEQ ID NO: 9), and a combination thereof.

4. The yeast cells of claim 1 or 2, wherein the polynucleotide sequence encoding the one or more epitopes of hemaglutinin is selected from the group consisting of: CTGTTG- GCGCCTGTTTACAGTCGC (SEQ ID NO: 1), AGGGGAGACGTGAGAGTGACGCCT (SEQ ID NO: 2), AACAAGTGTGTT (SEQ ID NO: 3), TTTTCGGTGAAG-GTGTTGACTTTC (SEQ ID NO: 4), ATCTACAAGGTCT-GCATTGCA (SEQ ID NO: 5), TTTGGGATTGCTCTGT-TCCTA (SEQ ID NO: 6), and a combination thereof.

5. The yeast cells of claim 1 or 2, wherein the polynucleotide sequence encoding the one or more epitopes of hemaglutinin is selected from the group consisting of: CTGTTG-GCGCCTGTTTACAGTCGC (SEQ ID NO: 1), AGGGGAGACGTGAGAGTGACGCCT (SEQ ID NO: 2), AACAAGTGTGTT (SEQ ID NO: 3), and a combination thereof.

6. Sub-viral particles (SVP) comprising a VP2 capsid protein of IPNV and one or more epitopes of hemaglutinin of ISAV, wherein the one or more epitopes of hemaglutinin comprise one or more amino add sequences selected from the group consisting of: LLAPVYSR (SEQ ID NO: 7), RGD-VRVTP (SEQ ID NO: 8), NKCV (SEQ ID NO: 9), FSVKV-LTF (SEQ ID NO: 10), IYKVCIA (SEQ ID. NO: 11), and FGIALFL (SEQ ID NO: 12).

7. Sub-viral particles (SVP) comprising a VP2 capsid protein of IPNV and one or more epitopes of hemaglutinin of ISAV, wherein the one or more epitopes of hemaglutinin is located at either amino acid position 252 or 286 of the VP2 capsid protein.

* * * * *

SEQUENCE LISTING

```
<160> NUMBER OF SEQ ID NOS: 35

<210> SEQ ID NO 1
<211> LENGTH: 24
<212> TYPE: DNA
<213> ORGANISM: Infectious salmon anemia virus

<400> SEQUENCE: 1
ctgttggcgc ctgtttacag tcgc                                          24

<210> SEQ ID NO 2
<211> LENGTH: 24
<212> TYPE: DNA
<213> ORGANISM: Infectious salmon anemia virus

<400> SEQUENCE: 2
aggggagacg tgagagtgac gcct                                          24

<210> SEQ ID NO 3
<211> LENGTH: 12
<212> TYPE: DNA
<213> ORGANISM: Infectious salmon anemia virus

<400> SEQUENCE: 3
```

```
aacaagtgtg tt                                                          12

<210> SEQ ID NO 4
<211> LENGTH: 24
<212> TYPE: DNA
<213> ORGANISM: Infectious salmon anemia virus

<400> SEQUENCE: 4
ttttcggtga aggtgttgac tttc                                             24

<210> SEQ ID NO 5
<211> LENGTH: 21
<212> TYPE: DNA
<213> ORGANISM: Infectious salmon anemia virus

<400> SEQUENCE: 5
atctacaagg tctgcattgc a                                                21

<210> SEQ ID NO 6
<211> LENGTH: 21
<212> TYPE: DNA
<213> ORGANISM: Infectious salmon anemia virus

<400> SEQUENCE: 6
tttgggattg ctctgttcct a                                                21

<210> SEQ ID NO 7
<211> LENGTH: 8
<212> TYPE: PRT
<213> ORGANISM: Infectious salmon anemia virus

<400> SEQUENCE: 7

Leu Leu Ala Pro Val Tyr Ser Arg
1               5

<210> SEQ ID NO 8
<211> LENGTH: 8
<212> TYPE: PRT
<213> ORGANISM: Infectious salmon anemia virus

<400> SEQUENCE: 8

Arg Gly Asp Val Arg Val Thr Pro
1               5

<210> SEQ ID NO 9
<211> LENGTH: 4
<212> TYPE: PRT
<213> ORGANISM: Infectious salmon anemia virus

<400> SEQUENCE: 9

Asn Lys Cys Val
1

<210> SEQ ID NO 10
<211> LENGTH: 8
<212> TYPE: PRT
<213> ORGANISM: Infectious salmon anemia virus

<400> SEQUENCE: 10

Phe Ser Val Lys Val Leu Thr Phe
1               5

<210> SEQ ID NO 11
<211> LENGTH: 7
```

```
<212> TYPE: PRT
<213> ORGANISM: Infectious salmon anemia virus

<400> SEQUENCE: 11

Ile Tyr Lys Val Cys Ile Ala
1               5

<210> SEQ ID NO 12
<211> LENGTH: 7
<212> TYPE: PRT
<213> ORGANISM: Infectious salmon anemia virus

<400> SEQUENCE: 12

Phe Gly Ile Ala Leu Phe Leu
1               5

<210> SEQ ID NO 13
<211> LENGTH: 35
<212> TYPE: DNA
<213> ORGANISM: Artificial Sequence
<220> FEATURE:
<223> OTHER INFORMATION: Completely Synthesized

<400> SEQUENCE: 13
cctgatgaga atgagactga cgcgggtcct ttggc                         35

<210> SEQ ID NO 14
<211> LENGTH: 39
<212> TYPE: DNA
<213> ORGANISM: Artificial Sequence
<220> FEATURE:
<223> OTHER INFORMATION: Completely Synthesized

<400> SEQUENCE: 14
ccctcaggac aaggtcaaca accaactagt gaccaaagg                     39

<210> SEQ ID NO 15
<211> LENGTH: 40
<212> TYPE: DNA
<213> ORGANISM: Artificial Sequence
<220> FEATURE:
<223> OTHER INFORMATION: Completely Synthesized

<400> SEQUENCE: 15
ctgttggcgc ctgtttacag tcgcaacgag acgcggttcg                    40

<210> SEQ ID NO 16
<211> LENGTH: 39
<212> TYPE: DNA
<213> ORGANISM: Artificial Sequence
<220> FEATURE:
<223> OTHER INFORMATION: Completely Synthesized

<400> SEQUENCE: 16
gcgactgtaa acaggcgcca acaggacggg ttcggctgc                     39

<210> SEQ ID NO 17
<211> LENGTH: 39
<212> TYPE: DNA
<213> ORGANISM: Artificial Sequence
<220> FEATURE:
<223> OTHER INFORMATION: Completely Synthesized

<400> SEQUENCE: 17
aggggagacg tgagagtgac gcctaacgag acgcggttc                     39
```

<210> SEQ ID NO 18
<211> LENGTH: 39
<212> TYPE: DNA
<213> ORGANISM: Artificial Sequence
<220> FEATURE:
<223> OTHER INFORMATION: Completely Synthesized

<400> SEQUENCE: 18
aggcgtcact ctcacgtctc ccctgacggg ttcggctgc                    39

<210> SEQ ID NO 19
<211> LENGTH: 37
<212> TYPE: DNA
<213> ORGANISM: Artificial Sequence
<220> FEATURE:
<223> OTHER INFORMATION: Completely Synthesized

<400> SEQUENCE: 19
aacaagtgtg ttgacgggtt cggctgctag ttggaag                      37

<210> SEQ ID NO 20
<211> LENGTH: 37
<212> TYPE: DNA
<213> ORGANISM: Artificial Sequence
<220> FEATURE:
<223> OTHER INFORMATION: Completely Synthesized

<400> SEQUENCE: 20
aacacacttg ttgacgggtt cggctgctag ttggaag                      37

<210> SEQ ID NO 21
<211> LENGTH: 39
<212> TYPE: DNA
<213> ORGANISM: Artificial Sequence
<220> FEATURE:
<223> OTHER INFORMATION: Completely Synthesized

<400> SEQUENCE: 21
ctgttggcgc ctgtttacag tcgctacagg ggtgcctcc                    39

<210> SEQ ID NO 22
<211> LENGTH: 39
<212> TYPE: DNA
<213> ORGANISM: Artificial Sequence
<220> FEATURE:
<223> OTHER INFORMATION: Completely Synthesized

<400> SEQUENCE: 22
gcgactgtaa acaggcgcca acaggttgtc ggccgtgac                    39

<210> SEQ ID NO 23
<211> LENGTH: 38
<212> TYPE: DNA
<213> ORGANISM: Artificial Sequence
<220> FEATURE:
<223> OTHER INFORMATION: Completely Synthesized

<400> SEQUENCE: 23
aggggagacg tgagagtgac gcctacaggg gtgcctcc                     38

<210> SEQ ID NO 24
<211> LENGTH: 39
<212> TYPE: DNA
<213> ORGANISM: Artificial Sequence
<220> FEATURE:
<223> OTHER INFORMATION: Completely Synthesized

```
<400> SEQUENCE: 24
aggcgtcact ctcacgtctc ccctgttgtc ggccgtgac                           39

<210> SEQ ID NO 25
<211> LENGTH: 38
<212> TYPE: DNA
<213> ORGANISM: Artificial Sequence
<220> FEATURE:
<223> OTHER INFORMATION: Completely Synthesized

<400> SEQUENCE: 25
aacaagtgtg ttgttgtcgg ccgtgaccag ggttgagc                            38

<210> SEQ ID NO 26
<211> LENGTH: 38
<212> TYPE: DNA
<213> ORGANISM: Artificial Sequence
<220> FEATURE:
<223> OTHER INFORMATION: Completely Synthesized

<400> SEQUENCE: 26
aacaagtgtg tttacagggg tgcctccgcc aagtttac                            38

<210> SEQ ID NO 27
<211> LENGTH: 16
<212> TYPE: PRT
<213> ORGANISM: Artificial Sequence
<220> FEATURE:
<223> OTHER INFORMATION: Completely Synthesized

<400> SEQUENCE: 27

Leu Leu Ala Pro Val Tyr Ser Arg Leu Leu Ala Pro Val Tyr Ser Arg
1               5                   10                  15

<210> SEQ ID NO 28
<211> LENGTH: 16
<212> TYPE: PRT
<213> ORGANISM: Artificial Sequence
<220> FEATURE:
<223> OTHER INFORMATION: Completely Synthesized

<400> SEQUENCE: 28

Arg Gly Asp Val Arg Val Thr Pro Arg Gly Asp Val Arg Val Thr Pro
1               5                   10                  15

<210> SEQ ID NO 29
<211> LENGTH: 16
<212> TYPE: PRT
<213> ORGANISM: Artificial Sequence
<220> FEATURE:
<223> OTHER INFORMATION: Completely Synthesized

<400> SEQUENCE: 29

Asn Lys Cys Val Asn Lys Cys Val Asn Lys Cys Val Asn Lys Cys Val
1               5                   10                  15

<210> SEQ ID NO 30
<211> LENGTH: 23
<212> TYPE: DNA
<213> ORGANISM: Artificial Sequence
<220> FEATURE:
<223> OTHER INFORMATION: Completely Synthesized

<400> SEQUENCE: 30
aggagatgac atgtgctaca ccg                                           23
```

```
<210> SEQ ID NO 31
<211> LENGTH: 22
<212> TYPE: DNA
<213> ORGANISM: Artificial Sequence
<220> FEATURE:
<223> OTHER INFORMATION: Completely Synthesized

<400> SEQUENCE: 31
ccagcgaata ttttctccac ca                                          22

<210> SEQ ID NO 32
<211> LENGTH: 21
<212> TYPE: DNA
<213> ORGANISM: Artificial Sequence
<220> FEATURE:
<223> OTHER INFORMATION: Completely Synthesized

<400> SEQUENCE: 32
tgcttcaccg ttccagttgt g                                           21

<210> SEQ ID NO 33
<211> LENGTH: 21
<212> TYPE: DNA
<213> ORGANISM: Artificial Sequence
<220> FEATURE:
<223> OTHER INFORMATION: Completely Synthesized

<400> SEQUENCE: 33
tgcttcaccg ttccagttgt g                                           21

<210> SEQ ID NO 34
<211> LENGTH: 21
<212> TYPE: DNA
<213> ORGANISM: Artificial Sequence
<220> FEATURE:
<223> OTHER INFORMATION: Completely Synthesized

<400> SEQUENCE: 34
tgatctacaa gtgcggaggc a                                           21

<210> SEQ ID NO 35
<211> LENGTH: 21
<212> TYPE: DNA
<213> ORGANISM: Artificial Sequence
<220> FEATURE:
<223> OTHER INFORMATION: Completely Synthesized

<400> SEQUENCE: 35
cagcacccag gcatacttga a                                           21
```